(12) United States Patent
Zucherman et al.

(10) Patent No.: US 8,070,778 B2
(45) Date of Patent: Dec. 6, 2011

(54) INTERSPINOUS PROCESS IMPLANT WITH SLIDE-IN DISTRACTION PIECE AND METHOD OF IMPLANTATION

(75) Inventors: James F. Zucherman, San Francisco, CA (US); Ken Y. Hsu, San Francisco, CA (US); Henry Klyce, Piedmont, CA (US); Charles J. Winslow, Walnut Creek, CA (US); Scott A. Yerby, Montara, CA (US); John J. Flynn, West Milford, NJ (US); Steve Mitchell, Pleasant Hill, CA (US); John A. Markwart, Castro Valley, CA (US)

(73) Assignee: Kyphon Sarl, Neuchatel (CH)

( * ) Notice: Subject to any disclaimer, the term of this patent is extended or adjusted under 35 U.S.C. 154(b) by 1201 days.

(21) Appl. No.: 11/378,893

(22) Filed: Mar. 17, 2006

(65) Prior Publication Data
US 2006/0265067 A1 Nov. 23, 2006

Related U.S. Application Data

(63) Continuation-in-part of application No. 10/850,267, filed on May 20, 2004, now Pat. No. 7,695,513.

(60) Provisional application No. 60/664,311, filed on Mar. 22, 2005, provisional application No. 60/472,817, filed on May 22, 2003.

(51) Int. Cl.
*A61B 17/70* (2006.01)
(52) U.S. Cl. ......................................... 606/248; 606/249
(58) Field of Classification Search .......... 606/246–279; 623/17.11–17.16
See application file for complete search history.

(56) References Cited

U.S. PATENT DOCUMENTS

| | | | |
|---|---|---|---|
| 624,969 A | 5/1899 | Peterson | |
| 1,153,797 A | 9/1915 | Kegreisz | |
| 1,516,347 A | 11/1924 | Pataky | |
| 1,870,942 A | 8/1932 | Beatty | |
| 2,077,804 A | 4/1937 | Morrison | |

(Continued)

FOREIGN PATENT DOCUMENTS

CA 2015507 1/1991
(Continued)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, (c) 1997, Lippincott-Raven Publishers.

(Continued)

*Primary Examiner* — Thomas C. Barrett
*Assistant Examiner* — Matthew Lawson

(57) ABSTRACT

Systems and method in accordance with embodiments of the present invention can includes an implant having an initiating piece and a distraction piece. The initiating piece can include a lower distraction element, a second wing, a lower portion of a spacer, and a lower portion of a first wing. The initiating piece can be positioned such that an interspinous ligament of the targeted motion segment is disposed between the first and second wing. The distraction piece can include an upper distraction element, an upper portion of the spacer, and an upper portion of the first wing, and can be mated with the initiating piece by mating a rail of the distraction piece with a slot of the initiating piece, thereby disposing the implant between adjacent spinous processes.

7 Claims, 20 Drawing Sheets

U.S. PATENT DOCUMENTS

| | | | |
|---|---|---|---|
| 2,299,308 A | 10/1942 | Creighton | |
| 2,456,806 A | 12/1948 | Wolffe | 33/174 |
| 2,485,531 A | 10/1949 | Dzus et al. | |
| 2,607,370 A | 8/1952 | Anderson | |
| 2,677,369 A | 5/1954 | Knowles | 128/92 |
| 2,685,877 A | 8/1954 | Dobelle | |
| 3,065,659 A | 11/1962 | Eriksson et al. | |
| 3,108,595 A | 10/1963 | Overment | |
| 3,426,364 A | 2/1969 | Lumb | 3/1 |
| 3,643,658 A | 2/1972 | Steinemenan | 128/920 |
| 3,648,691 A | 3/1972 | Lumb | 128/920 |
| 3,779,239 A | 12/1973 | Fischer et al. | |
| 3,867,728 A | 2/1975 | Stubstad | 3/1 |
| 3,875,595 A | 4/1975 | Froning | 3/1 |
| 4,011,602 A | 3/1977 | Rybicki et al. | |
| 4,034,418 A | 7/1977 | Jackson | 3/1.911 |
| 4,219,015 A | 8/1980 | Steinemenan | 128/92 D |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,309,777 A | 1/1982 | Patil | 3/1.91 |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |
| 4,455,690 A | 6/1984 | Homsy | 3/1 |
| 4,479,491 A | 10/1984 | Martin | 128/92 B |
| 4,501,269 A | 2/1985 | Bagby | 128/96 G |
| 4,502,161 A | 3/1985 | Wall | 623/18 |
| 4,519,100 A | 5/1985 | Wills et al. | |
| 4,553,273 A | 11/1985 | Wu | 623/18 |
| 4,554,914 A | 11/1985 | Kapp | 128/92 C |
| 4,573,454 A | 3/1986 | Hoffman | |
| 4,592,341 A | 6/1986 | Omagari et al. | |
| 4,599,084 A | 7/1986 | Nashef | 623/16 |
| 4,599,086 A * | 7/1986 | Doty | 606/86 A |
| 4,604,995 A | 8/1986 | Stephens | 128/69 |
| 4,611,582 A | 9/1986 | Duff | 128/69 |
| 4,632,101 A | 12/1986 | Freedland | |
| 4,636,217 A | 1/1987 | Ogilvie | 623/17 |
| 4,643,178 A | 2/1987 | Nastari | 128/92 |
| 4,646,998 A | 3/1987 | Pate | |
| 4,657,550 A | 4/1987 | Daher | 623/17 |
| 4,662,808 A | 5/1987 | Camilleri | |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,704,057 A | 11/1987 | McSherry | |
| 4,714,469 A | 12/1987 | Kenna | 623/17 |
| 4,743,256 A | 5/1988 | Brantigan | 623/17 |
| 4,759,769 A | 7/1988 | Hedman et al. | |
| 4,772,287 A | 9/1988 | Ray | 623/17 |
| 4,787,378 A | 11/1988 | Sodhi | |
| 4,790,303 A | 12/1988 | Steffee | 128/924 M |
| 4,822,226 A | 4/1989 | Kennedy | |
| 4,827,918 A | 5/1989 | Olerud | |
| 4,834,600 A | 5/1989 | Lemke | |
| 4,834,757 A | 5/1989 | Brantigan | 623/17 |
| 4,863,476 A | 9/1989 | Shepperd | |
| 4,878,915 A | 11/1989 | Brantigan | 623/17 |
| 4,886,405 A | 12/1989 | Blomberg | |
| 4,892,545 A | 1/1990 | Day et al. | |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,913,144 A * | 4/1990 | Del Medico | 606/75 |
| 4,923,471 A | 5/1990 | Morgan | 623/16 |
| 4,931,055 A | 6/1990 | Bumpus et al. | |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,887 A | 11/1990 | Sodhi | |
| 4,969,888 A | 11/1990 | Scholten | 606/94 |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,098,433 A | 3/1992 | Freedland | |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,171,278 A | 12/1992 | Pisharodi | |
| 5,180,381 A | 1/1993 | Aust | 606/61 |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,275,601 A | 1/1994 | Gogolewski | 606/72 |
| 5,290,312 A * | 3/1994 | Kojimoto et al. | 623/17.15 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,306,310 A | 4/1994 | Siebels | |
| 5,312,405 A | 5/1994 | Korotko et al. | |
| 5,352,225 A | 10/1994 | Yuan | 606/61 |
| 5,360,430 A | 11/1994 | Lin | |
| 5,366,455 A | 11/1994 | Dove | 606/61 |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,370 A | 3/1995 | Muller et al. | |
| 5,395,372 A | 3/1995 | Holt | 606/61 |
| 5,401,269 A | 3/1995 | Buttner-Janz et al. | |
| 5,403,316 A | 4/1995 | Ashman | |
| 5,415,661 A | 5/1995 | Holmes | 606/69 |
| 5,437,672 A | 8/1995 | Alleyne | 606/61 |
| 5,437,674 A | 8/1995 | Worcel et al. | |
| 5,439,463 A | 8/1995 | Lin | |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,491,882 A | 2/1996 | Walston | 29/419.1 |
| 5,496,318 A | 3/1996 | Howland | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,518,498 A | 5/1996 | Lindenberg et al. | |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,662 A | 10/1996 | Brumfield et al. | |
| 5,562,735 A | 10/1996 | Margulies | |
| 5,562,736 A | 10/1996 | Ray | 623/17 |
| 5,571,191 A | 11/1996 | Fitz | 623/17 |
| 5,571,192 A | 11/1996 | Schonhoffer | |
| 5,577,995 A | 11/1996 | Walker | 601/120 |
| 5,584,832 A | 12/1996 | Schlapfer | 606/61 |
| 5,593,409 A | 1/1997 | Michelson | 606/61 |
| 5,601,553 A | 2/1997 | Trebing | 606/61 |
| 5,603,713 A * | 2/1997 | Aust et al. | 606/279 |

| Patent No. | Kind | Date | Inventor | Class |
|---|---|---|---|---|
| 5,609,634 | A | 3/1997 | Voydeville | 623/17 |
| 5,609,635 | A | 3/1997 | Michelson | |
| 5,616,142 | A | 4/1997 | Yuan | 606/61 |
| 5,623,984 | A | 4/1997 | Nozaki | 164/457 |
| 5,628,756 | A | 5/1997 | Barker, Jr. | 606/139 |
| 5,630,816 | A | 5/1997 | Kambin | |
| 5,645,597 | A | 7/1997 | Krapiva | 623/17 |
| 5,645,599 | A | 7/1997 | Samani | 623/17 |
| 5,653,761 | A | 8/1997 | Pisharodi | 623/17 |
| 5,653,762 | A | 8/1997 | Pisharodi | |
| 5,653,763 | A | 8/1997 | Errico et al. | |
| 5,658,286 | A | 8/1997 | Sava | 606/61 |
| 5,658,335 | A | 8/1997 | Allen | |
| 5,665,122 | A | 9/1997 | Kambin | |
| 5,672,177 | A | 9/1997 | Seldin | 606/71 |
| 5,674,295 | A | 10/1997 | Ray | 623/17 |
| 5,674,296 | A | 10/1997 | Bryan | 623/17 |
| 5,676,702 | A | 10/1997 | Ratron | 623/17 |
| 5,685,826 | A | 11/1997 | Bonutti | |
| 5,690,649 | A | 11/1997 | Li | |
| 5,693,100 | A | 12/1997 | Pisharodi | |
| 5,702,395 | A | 12/1997 | Hopf | |
| 5,702,452 | A | 12/1997 | Argenson et al. | |
| 5,702,455 | A | 12/1997 | Saggar | 623/17 |
| 5,707,390 | A | 1/1998 | Bonutti | |
| 5,716,416 | A | 2/1998 | Lin | |
| 5,723,013 | A * | 3/1998 | Jeanson et al. | 623/17.16 |
| 5,725,341 | A | 3/1998 | Hofmeister | |
| 5,725,582 | A | 3/1998 | Bevan | 623/17 |
| 5,741,261 | A | 4/1998 | Moskovitz | 606/79 |
| 5,746,762 | A | 5/1998 | Bass | |
| 5,755,797 | A | 5/1998 | Baumgartner | |
| 5,766,251 | A | 6/1998 | Koshino | 623/16 |
| 5,766,252 | A | 6/1998 | Henry | 623/17 |
| 5,800,438 | A | 9/1998 | Tuke | 606/90 |
| 5,800,547 | A | 9/1998 | Schafer et al. | |
| 5,810,815 | A | 9/1998 | Morales | |
| 5,824,098 | A | 10/1998 | Stein | 623/20 |
| 5,836,948 | A | 11/1998 | Zucherman | 606/61 |
| 5,849,004 | A | 12/1998 | Bramlet | |
| 5,860,977 | A | 1/1999 | Zucherman | 606/61 |
| 5,865,846 | A | 2/1999 | Bryan | 623/17 |
| 5,876,402 | A | 3/1999 | Errico | 606/61 |
| 5,876,404 | A | 3/1999 | Zucherman | 606/61 |
| 5,879,396 | A | 3/1999 | Walston | 623/21 |
| 5,885,299 | A | 3/1999 | Winslow | 606/99 |
| 5,888,196 | A | 3/1999 | Bonutti | |
| 5,888,224 | A | 3/1999 | Beckers | 627/17 |
| 5,888,226 | A | 3/1999 | Rogozinski | 623/17 |
| 5,951,555 | A | 9/1999 | Rehak | 606/61 |
| 5,976,186 | A | 11/1999 | Bao | 623/17 |
| 5,980,523 | A | 11/1999 | Jackson | |
| 6,001,130 | A | 12/1999 | Bryan | 623/17 |
| 6,022,376 | A | 2/2000 | Assell | 623/17 |
| 6,030,162 | A | 2/2000 | Huebner | 411/413 |
| 6,045,552 | A | 4/2000 | Zucherman | 606/61 |
| 6,045,554 | A | 4/2000 | Grooms | 606/73 |
| 6,048,204 | A | 4/2000 | Klardie | 433/174 |
| 6,048,342 | A * | 4/2000 | Zucherman et al. | 606/249 |
| 6,048,344 | A | 4/2000 | Schenk | 606/73 |
| 6,068,630 | A | 5/2000 | Zucherman | 606/61 |
| RE36,758 | E | 6/2000 | Fitz | 623/17 |
| 6,074,390 | A | 6/2000 | Zucherman | 606/61 |
| 6,090,112 | A | 7/2000 | Zucherman | 606/61 |
| 6,099,531 | A | 8/2000 | Bonutti | 606/87 |
| 6,113,639 | A | 9/2000 | Ray | 623/17.16 |
| 6,126,689 | A | 10/2000 | Brett | |
| 6,126,691 | A | 10/2000 | Kasra et al. | |
| 6,127,597 | A | 10/2000 | Beyar et al. | |
| 6,129,730 | A | 10/2000 | Bono | 606/73 |
| 6,132,464 | A | 10/2000 | Martin | 623/17 |
| 6,139,550 | A | 10/2000 | Michelson | 606/61 |
| 6,149,652 | A | 11/2000 | Zucherman | 606/61 |
| 6,152,926 | A | 11/2000 | Zucherman | 606/61 |
| 6,152,927 | A | 11/2000 | Farris | 606/69 |
| 6,156,038 | A | 12/2000 | Zucherman | 606/61 |
| 6,156,067 | A | 12/2000 | Bryan | 623/17.15 |
| 6,183,471 | B1 | 2/2001 | Zucherman | 606/61 |
| 6,190,387 | B1 | 2/2001 | Zucherman | 606/61 |
| 6,190,413 | B1 | 2/2001 | Sutcliffe | |
| 6,190,414 | B1 | 2/2001 | Young | 623/17.15 |
| 6,193,721 | B1 | 2/2001 | Michelson | 606/70 |
| 6,200,322 | B1 | 3/2001 | Branch | 606/96 |
| 6,206,922 | B1 | 3/2001 | Zdeblick | 623/17.11 |
| 6,214,050 | B1 | 4/2001 | Huene | |
| 6,217,580 | B1 | 4/2001 | Levin | 606/71 |
| 6,224,602 | B1 | 5/2001 | Hayes | 606/69 |
| 6,224,607 | B1 | 5/2001 | Michelson | 606/96 |
| 6,228,900 | B1 | 5/2001 | Shen | 522/153 |
| 6,234,705 | B1 | 5/2001 | Troxell | 403/237 |
| 6,235,030 | B1 | 5/2001 | Zucherman | 606/61 |
| 6,238,397 | B1 | 5/2001 | Zucherman | 606/61 |
| 6,261,296 | B1 | 7/2001 | Aebi | 606/90 |
| 6,280,444 | B1 | 8/2001 | Zucherman | 606/61 |
| 6,293,949 | B1 | 9/2001 | Justis | 606/61 |
| 6,306,136 | B1 | 10/2001 | Baccelli | 606/61 |
| 6,332,882 | B1 | 12/2001 | Zucherman | 606/61 |
| 6,332,883 | B1 | 12/2001 | Zucherman | 606/61 |
| 6,336,930 | B1 | 1/2002 | Stalcup et al. | |
| 6,348,053 | B1 | 2/2002 | Cachia | |
| 6,352,537 | B1 | 3/2002 | Strnad | 606/61 |
| 6,364,883 | B1 | 4/2002 | Santilli | |
| 6,368,351 | B1 | 4/2002 | Glenn | 623/17.15 |
| 6,371,984 | B1 | 4/2002 | Van Dyke | 623/11.11 |
| 6,371,987 | B1 | 4/2002 | Weiland et al. | |
| 6,375,682 | B1 | 4/2002 | Fleischmann et al. | |
| 6,379,355 | B1 | 4/2002 | Zucherman | 606/61 |
| 6,383,186 | B1 | 5/2002 | Michelson | 606/69 |
| 6,395,030 | B1 | 5/2002 | Songer | 623/17.11 |
| 6,398,783 | B1 | 6/2002 | Michelson | 606/70 |
| 6,402,750 | B1 | 6/2002 | Atkinson et al. | |
| 6,402,751 | B1 | 6/2002 | Hoeck et al. | |
| 6,402,756 | B1 | 6/2002 | Ralph | 606/71 |
| 6,416,776 | B1 | 7/2002 | Shamie | 424/423 |
| 6,419,676 | B1 | 7/2002 | Zucherman | 606/61 |
| 6,419,677 | B2 | 7/2002 | Zucherman | 606/61 |
| 6,419,703 | B1 | 7/2002 | Fallin | 623/17.11 |
| 6,419,704 | B1 | 7/2002 | Ferree | |
| 6,428,542 | B1 | 8/2002 | Michelson | 606/70 |
| 6,436,145 | B1 | 8/2002 | Miller | 623/20.34 |
| 6,440,169 | B1 | 8/2002 | Elberg et al. | 623/17.16 |
| 6,447,513 | B1 | 9/2002 | Griggs | |
| 6,451,019 | B1 | 9/2002 | Zucherman | 606/61 |
| 6,451,020 | B1 | 9/2002 | Zucherman | 606/61 |
| 6,454,771 | B1 | 9/2002 | Michelson | 606/70 |
| 6,458,131 | B1 | 10/2002 | Ray | 606/61 |
| 6,478,796 | B1 | 11/2002 | Zucherman | 606/61 |
| 6,500,178 | B2 | 12/2002 | Zucherman | 606/61 |
| 6,514,256 | B2 | 2/2003 | Zucherman | 606/61 |
| 6,520,991 | B2 | 2/2003 | Huene | |
| 6,527,776 | B1 | 3/2003 | Michelson | 606/70 |
| 6,554,833 | B2 | 4/2003 | Levy | |
| 6,558,423 | B1 | 5/2003 | Michelson | 623/17.11 |
| 6,558,686 | B1 | 5/2003 | Darouiche | 424/423 |
| 6,565,570 | B2 | 5/2003 | Sterett | 606/69 |
| 6,565,605 | B2 | 5/2003 | Goble | 623/17.11 |
| 6,579,318 | B2 | 6/2003 | Varga | 623/17.11 |
| 6,579,319 | B2 | 6/2003 | Goble | 623/17.11 |
| 6,582,433 | B2 | 6/2003 | Yun | 606/61 |
| 6,582,467 | B1 | 6/2003 | Teitelbaum et al. | |
| 6,592,585 | B2 | 7/2003 | Lee et al. | |
| 6,592,586 | B1 | 7/2003 | Michelson | 606/71 |
| 6,610,091 | B1 | 8/2003 | Reiley | 623/17.11 |
| 6,620,163 | B1 | 9/2003 | Michelson | 606/61 |
| 6,626,944 | B1 | 9/2003 | Taylor | 623/17.16 |
| 6,641,585 | B2 | 11/2003 | Sato et al. | 606/61 |
| 6,645,207 | B2 | 11/2003 | Dixon et al. | |
| 6,652,527 | B2 | 11/2003 | Zucherman | 606/61 |
| 6,652,534 | B2 | 11/2003 | Zucherman | 606/102 |
| 6,669,729 | B2 | 12/2003 | Chin | 623/17.11 |
| 6,685,742 | B2 | 2/2004 | Jackson | |
| 6,695,842 | B2 | 2/2004 | Zucherman | 606/61 |
| 6,699,246 | B2 | 3/2004 | Zucherman | 606/61 |
| 6,699,247 | B2 | 3/2004 | Zucherman | 606/61 |
| 6,709,435 | B2 | 3/2004 | Lin | |
| 6,712,819 | B2 | 3/2004 | Zucherman | 606/61 |
| 6,712,852 | B1 | 3/2004 | Chung | 623/17.11 |
| 6,723,126 | B1 | 4/2004 | Berry | |

| Patent Number | Date | Inventor(s) | Class |
|---|---|---|---|
| 6,730,126 B2 | 5/2004 | Boehm, Jr. et al. | |
| 6,730,127 B2 | 5/2004 | Michelson | 623/17.16 |
| 6,733,534 B2 | 5/2004 | Sherman | |
| 6,736,818 B2 | 5/2004 | Perren et al. | |
| 6,743,257 B2 | 6/2004 | Castro | |
| 6,746,485 B1 | 6/2004 | Zucherman | 623/17.16 |
| 6,752,831 B2 | 6/2004 | Sybert | 623/13.17 |
| 6,758,863 B2 | 7/2004 | Estes et al. | |
| 6,761,720 B1 | 7/2004 | Senegas | 606/61 |
| 6,764,491 B2 | 7/2004 | Frey et al. | 606/85 |
| 6,770,096 B2 | 8/2004 | Bolger et al. | |
| 6,783,527 B2 | 8/2004 | Drewry | 606/61 |
| 6,783,530 B1 | 8/2004 | Levy | |
| 6,796,983 B1 | 9/2004 | Zucherman | 606/61 |
| 6,800,670 B2 | 10/2004 | Shen | 522/153 |
| 6,811,567 B2 | 11/2004 | Reiley | 623/17.11 |
| 6,835,205 B2 | 12/2004 | Atkinson et al. | |
| 6,902,566 B2 | 6/2005 | Zucherman | 606/61 |
| 6,905,512 B2 | 6/2005 | Paes et al. | |
| 6,926,728 B2 | 8/2005 | Zucherman et al. | 606/190 |
| 6,936,050 B2 | 8/2005 | Michelson | 606/61 |
| 6,936,051 B2 | 8/2005 | Michelson | 606/61 |
| 6,946,000 B2 | 9/2005 | Senegas et al. | |
| 6,949,123 B2 | 9/2005 | Reiley | 623/17.11 |
| 6,969,390 B2 | 11/2005 | Michelson | 606/61 |
| 6,972,019 B2 | 12/2005 | Michelson | 606/61 |
| 6,974,478 B2 | 12/2005 | Reiley et al. | 623/17.11 |
| 6,981,975 B2 | 1/2006 | Michelson | |
| 7,011,685 B2 * | 3/2006 | Arnin et al. | 623/17.16 |
| 7,025,789 B2 | 4/2006 | Chow et al. | 623/21.11 |
| 7,041,105 B2 | 5/2006 | Michelson | 606/71 |
| 7,041,135 B2 | 5/2006 | Michelson | 623/17.11 |
| 7,041,136 B2 | 5/2006 | Goble et al. | 623/17.11 |
| 7,044,952 B2 | 5/2006 | Michelson | 606/71 |
| 7,048,736 B2 | 5/2006 | Robinson et al. | 606/61 |
| 7,063,701 B2 | 6/2006 | Michelson | 606/73 |
| 7,063,702 B2 | 6/2006 | Michelson | 606/73 |
| 7,074,237 B2 | 7/2006 | Goble et al. | 623/17.11 |
| 7,077,844 B2 | 7/2006 | Michelson | 606/71 |
| 7,081,120 B2 | 7/2006 | Li et al. | |
| 7,087,083 B2 | 8/2006 | Pasquet et al. | |
| 7,087,084 B2 | 8/2006 | Reiley | 623/17.11 |
| 7,090,698 B2 | 8/2006 | Goble et al. | 623/17.11 |
| 7,097,645 B2 | 8/2006 | Michelson | 606/71 |
| 7,097,648 B1 | 8/2006 | Globerman et al. | |
| 7,101,375 B2 | 9/2006 | Zucherman et al. | 606/61 |
| 7,101,398 B2 | 9/2006 | Dooris et al. | 623/13.11 |
| 7,112,202 B2 | 9/2006 | Michelson | 606/71 |
| 7,115,130 B2 | 10/2006 | Michelson | 606/71 |
| 7,163,558 B2 | 1/2007 | Senegas et al. | |
| 7,163,561 B2 | 1/2007 | Michelson | 623/17.16 |
| 7,201,751 B2 | 4/2007 | Zucherman et al. | |
| 7,217,293 B2 | 5/2007 | Branch, Jr. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,377,942 B2 | 5/2008 | Berry | |
| 7,442,208 B2 | 10/2008 | Mathieu et al. | |
| 7,445,637 B2 | 11/2008 | Taylor | |
| 7,458,981 B2 | 12/2008 | Fielding et al. | |
| 7,582,106 B2 | 9/2009 | Teitelbaum et al. | |
| 7,604,652 B2 | 10/2009 | Arnin et al. | |
| 7,611,316 B2 | 11/2009 | Panasik et al. | |
| 2001/0016743 A1 | 8/2001 | Zucherman et al. | |
| 2001/0018614 A1 | 8/2001 | Bianchi | |
| 2002/0133155 A1 | 9/2002 | Ferree | |
| 2002/0143331 A1 | 10/2002 | Zucherman et al. | |
| 2002/0151895 A1 | 10/2002 | Soboleski | |
| 2002/0183756 A1 | 12/2002 | Michelson | |
| 2003/0040746 A1 | 2/2003 | Mitchell | |
| 2003/0045940 A1 | 3/2003 | Eberlein et al. | |
| 2003/0065330 A1 | 4/2003 | Zucherman et al. | |
| 2003/0153915 A1 | 8/2003 | Nekozuka et al. | |
| 2004/0006391 A1 | 1/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0087947 A1 | 5/2004 | Lim et al. | |
| 2004/0087948 A1 | 5/2004 | Suddaby | |
| 2004/0097931 A1 | 5/2004 | Mitchell | |
| 2004/0116927 A1 | 6/2004 | Graf | |
| 2004/0122427 A1 | 6/2004 | Holmes | |
| 2004/0133204 A1 | 7/2004 | Davies | |
| 2004/0133280 A1 | 7/2004 | Trieu | |
| 2004/0143268 A1 | 7/2004 | Falahee | |
| 2004/0167625 A1 | 8/2004 | Beyar et al. | |
| 2004/0181229 A1 | 9/2004 | Michelson | |
| 2004/0186475 A1 | 9/2004 | Falahee | |
| 2004/0199255 A1 | 10/2004 | Mathieu et al. | |
| 2004/0210313 A1 | 10/2004 | Michelson | |
| 2004/0230201 A1 | 11/2004 | Yuan | |
| 2004/0230304 A1 | 11/2004 | Yuan | |
| 2004/0236334 A1 | 11/2004 | Michelson | |
| 2004/0236335 A1 | 11/2004 | Michelson | |
| 2004/0260397 A1 | 12/2004 | Lambrecht et al. | |
| 2005/0010293 A1 | 1/2005 | Zucherman et al. | |
| 2005/0027297 A1 | 2/2005 | Michelson | |
| 2005/0027298 A1 | 2/2005 | Michelson | |
| 2005/0049708 A1 | 3/2005 | Atkinson et al. | |
| 2005/0085814 A1 | 4/2005 | Sherman et al. | |
| 2005/0165398 A1 | 7/2005 | Reiley | |
| 2005/0203512 A1 | 9/2005 | Hawkins et al. | |
| 2005/0203519 A1 | 9/2005 | Harms et al. | |
| 2005/0203624 A1 | 9/2005 | Serhan et al. | |
| 2005/0228391 A1 | 10/2005 | Levy et al. | |
| 2005/0245937 A1 | 11/2005 | Winslow | |
| 2005/0261768 A1 | 11/2005 | Trieu | |
| 2005/0273166 A1 | 12/2005 | Sweeney | |
| 2005/0288672 A1 | 12/2005 | Feree | |
| 2006/0004447 A1 | 1/2006 | Mastrorio et al. | |
| 2006/0004455 A1 | 1/2006 | Leonard et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0095136 A1 | 5/2006 | McLuen | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |
| 2006/0129239 A1 | 6/2006 | Kwak | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0224241 A1 | 10/2006 | Butler et al. | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241613 A1 | 10/2006 | Bruneau et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0282079 A1 | 12/2006 | Labrom et al. | |
| 2006/0293662 A1 | 12/2006 | Boyer, II et al. | |
| 2006/0293663 A1 | 12/2006 | Walkenhorst et al. | |
| 2007/0005064 A1 | 1/2007 | Anderson et al. | |
| 2007/0032790 A1 | 2/2007 | Aschmann et al. | |
| 2007/0043362 A1 | 2/2007 | Malandain et al. | |
| 2007/0100340 A1 | 5/2007 | Lange et al. | |
| 2007/0123861 A1 | 5/2007 | Dewey et al. | |

| | | | |
|---|---|---|---|
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183211 A1 | 7/2008 | Lamborne et al. | |
| 2008/0183218 A1 | 7/2008 | Mueller et al. | |
| 2008/0215094 A1 | 9/2008 | Taylor | |
| 2008/0221685 A9 | 9/2008 | Altarac et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105773 A1 | 4/2009 | Lange et al. | |
| 2009/0234389 A1 | 9/2009 | Chuang et al. | |
| 2009/0270918 A1 | 10/2009 | Attia et al. | |
| 2010/0121379 A1 | 5/2010 | Edmond | |

FOREIGN PATENT DOCUMENTS

| | | |
|---|---|---|
| DE | 2821678 A1 | 11/1979 |
| DE | 2821678 A1 | 4/1980 |
| DE | 3113142 A1 | 1/1982 |
| DE | 3922044 A1 | 2/1991 |
| DE | 4012622 C1 | 7/1991 |
| DE | 4409833 | 10/1995 |
| DE | 4414781 | 11/1995 |
| DE | 201 12 123 U1 | 9/2001 |
| DE | 101 35 771 A1 | 2/2003 |
| EP | 140790 A2 | 10/1984 |
| EP | 146347 A1 | 12/1984 |
| EP | 322334 A1 | 12/1988 |
| EP | 0322334 B1 | 2/1992 |
| EP | 0307241 B1 | 12/1992 |
| EP | 0677277 A2 | 10/1995 |
| EP | 0767636 B1 | 4/1997 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1854433 A1 | 11/2007 |
| EP | 1982664 A1 | 10/2008 |
| FR | 2623085 | 5/1989 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2705227 | 11/1994 |
| FR | 2707864 A1 | 1/1995 |
| FR | 2717066 | 9/1995 |
| FR | 2717068 | 9/1995 |
| FR | 2717675 | 9/1995 |
| FR | 2717675 A1 | 9/1995 |
| FR | 2722087 A1 | 1/1996 |
| FR | 2722088 | 1/1996 |
| FR | 2722088 A1 | 1/1996 |
| FR | 2722980 A1 | 2/1996 |
| FR | 2724554 | 3/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2780269 A1 | 12/1999 |
| FR | 2782911 A1 | 3/2000 |
| FR | 2799948 A1 | 4/2001 |
| FR | 2806614 A1 | 9/2001 |
| FR | 2806616 A1 | 9/2001 |
| FR | 2816197 A1 | 5/2002 |
| GB | 780652 | 8/1957 |
| JP | 02-224660 | 9/1990 |
| JP | 09-075381 | 3/1997 |
| JP | 10-179622 | 7/1998 |
| SU | 988281 | 1/1983 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 94/26193 | 11/1994 |
| WO | WO 94/26195 | 11/1994 |
| WO | WO 95/35067 | 12/1995 |
| WO | WO 96/08206 A1 | 3/1996 |
| WO | WO 96/39975 | 12/1996 |
| WO | WO 97/18769 | 5/1997 |
| WO | WO 98/20939 | 5/1998 |
| WO | WO 98/48717 | 11/1998 |
| WO | WO 98/55038 | 12/1998 |
| WO | WO 99/26562 | 6/1999 |
| WO | WO 99/40866 | 8/1999 |
| WO | WO 99/42051 | 8/1999 |
| WO | WO 99/56653 | 11/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/38582 | 7/2000 |
| WO | WO 00/44319 | 8/2000 |
| WO | WO 00/53126 | 9/2000 |
| WO | WO 01/26566 A1 | 4/2001 |
| WO | WO 01/28442 A1 | 4/2001 |
| WO | WO 01/54598 A1 | 8/2001 |
| WO | WO 02/34120 A2 | 5/2002 |
| WO | WO 02/051326 | 7/2002 |
| WO | WO 02/085226 A1 | 10/2002 |
| WO | WO 03/057055 A1 | 7/2003 |
| WO | WO 03/101350 A1 | 12/2003 |
| WO | WO 2004/047689 A1 | 6/2004 |
| WO | WO 2004/047691 A1 | 6/2004 |
| WO | WO 2004/071358 A1 | 8/2004 |
| WO | WO 2004/084768 A2 | 10/2004 |
| WO | WO 2004/098465 A1 | 11/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |

| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Haruo Tsuji, et al., *Ceramic Interspinous Block (CISB) Assisted Anterior Interbody Fusion*, Journal of Spinal Disorders, vol. 3, No. 1, pp. 77-86, (c)1990 Raven Press, Ltd., New York.

Richard W. Porter, MD, FRCS, FRCSE, *Spinal Stenosis and Neurogenic Claudication*, SPINE vol. 21, No. 17, pp. 2046-2052, (c)1996, Lippincott-Raven Publishers.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DLAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases; Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

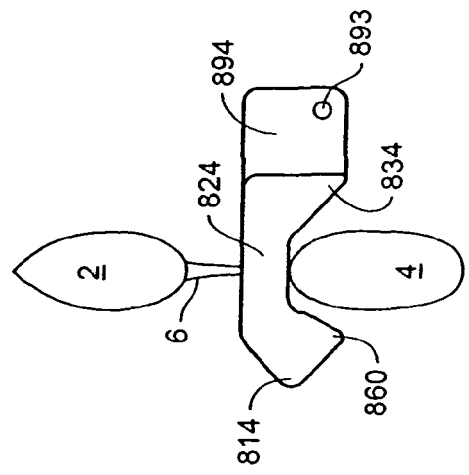
FIG. - 19C
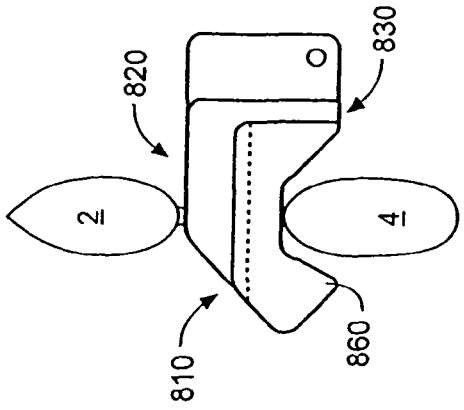
FIG. - 19E
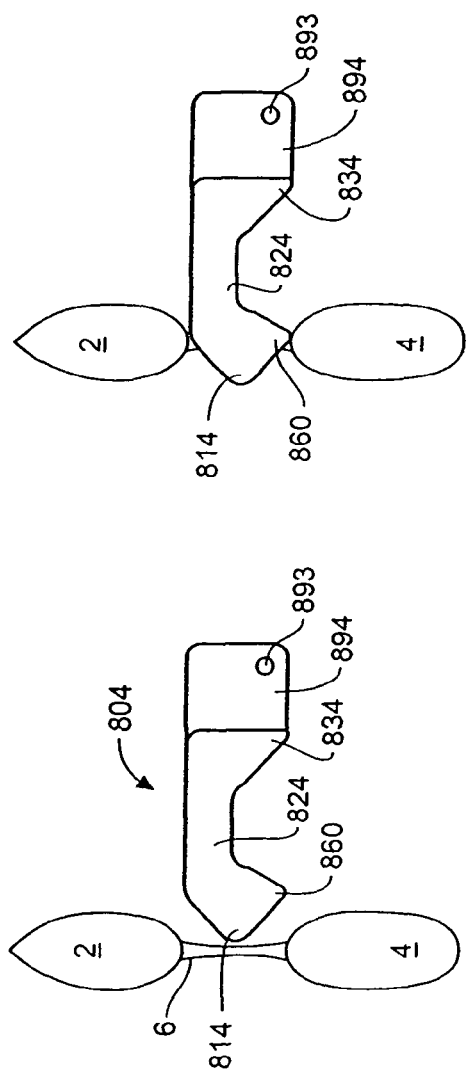
FIG. - 19B
FIG. - 19A
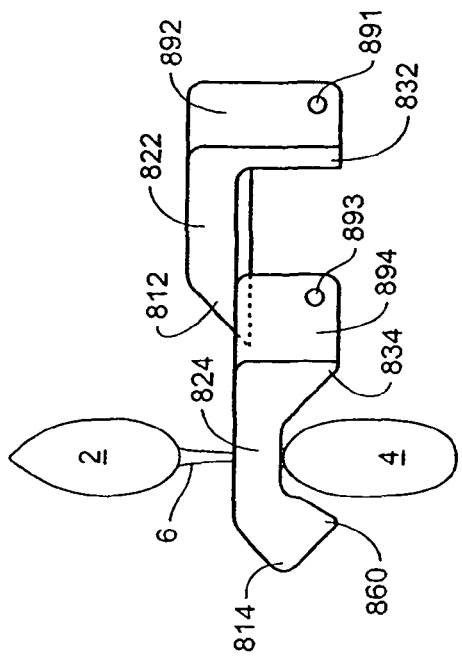
FIG. - 19D

INTERSPINOUS PROCESS IMPLANT WITH SLIDE-IN DISTRACTION PIECE AND METHOD OF IMPLANTATION

CLAIM OF PRIORITY

This application claims priority to U.S. Provisional Application No. 60/664,311 entitled INTERSPINOUS PROCESS IMPLANT WITH SLIDE-IN DISTRACTION PIECE AND METHOD OF IMPLANTATION, by Zucherman et al., filed Mar. 22, 2005, and is a continuation-in-part of U.S. patent application Ser. No. 10/850,267 entitled DISTRACTIBLE INTERSPINOUS PROCESS IMPLANT AND METHOD OF IMPLANTATION, by Zucherman et al., filed May 20, 2004, which claims priority to U.S. Provisional Patent Application No. 60/472,817 entitled CERVICAL INTERSPINOUS PROCESS DISTRACTION IMPLANT AND METHOD OF IMPLANTATION, by Zucherman et al., filed May 22, 2003.

CROSS-REFERENCE TO RELATED APPLICATIONS

This U.S. Patent Application incorporates by reference all of the following co-pending applications and issued patents:

U.S. Patent Application Serial No. 60/664,049, entitled "Interspinous Process Implant With Slide-In Distraction Piece and Method of Implantation," filed concurrently;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al;

U.S. Pat. No. 6,695,842, entitled "Interspinous Process Distraction System and Method with Positionable Wing and Method," issued Feb. 24, 2004 to Zucherman, et al;

U.S. Pat. No. 6,699,246, entitled "Spine Distraction Implant," issued Mar. 2, 2004 to Zucherman, et al; and U.S. Pat. No. 6,712,819, entitled "Mating Insertion Instruments for Spinal Implants and Methods of Use," issued Mar. 30, 2004 to Zucherman, et al.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the cervical nerve roots and causes radicular pain. Humpreys, S. C. et al., *Flexion and traction effect on C5-C6 foraminal space*, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., *Effect of cervical spine motion on the neuroforaminal dimensions of human cervical spine*, Spine, vol. 17 at 1131 (Nov. 10, 1992). In contrast, neck flexion increases the foraminal area. Humpreys, S. C. et al., at 1105.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the cervical spine. Such implants would distract, or increase the space between, the vertebrae to increase the foraminal area and reduce pressure on the nerves and blood vessels of the cervical spine.

A further need exists for development of a minimally invasive surgical implantation method for cervical spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

BRIEF DESCRIPTION OF THE DRAWINGS

Further details of embodiments of the present invention are explained with the help of the attached drawings in which:

FIGS. 19A-19C are posterior views of the initiating piece of FIG. 18A as the initiating piece is urged in position with the interspinous ligament disposed between the first wing and the second wing.

FIGS. 19D and 19E are posterior views showing the distraction piece of FIG. 18A urged so that the distraction piece is mated with the initiating piece.

DETAILED DESCRIPTION

Interspinous Implants

Figure 1:
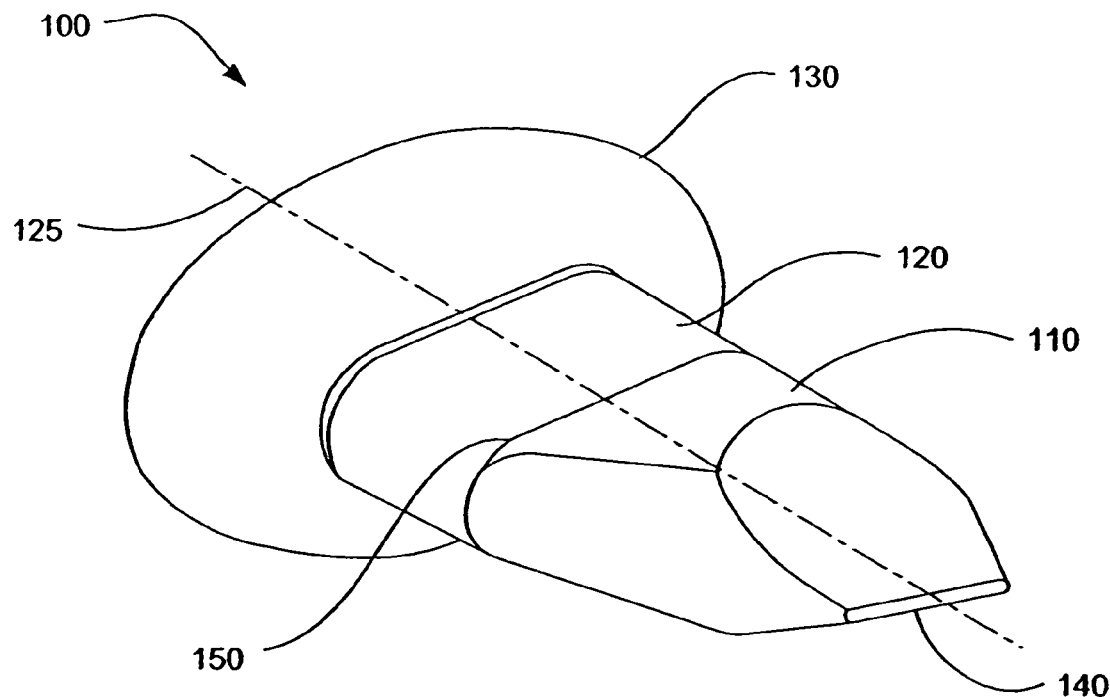
FIG. 1 is a perspective view of an embodiment of an implant in accordance with the present invention having a spacer, a distraction guide, and a wing with an elliptical cross-section.
Figure 2:
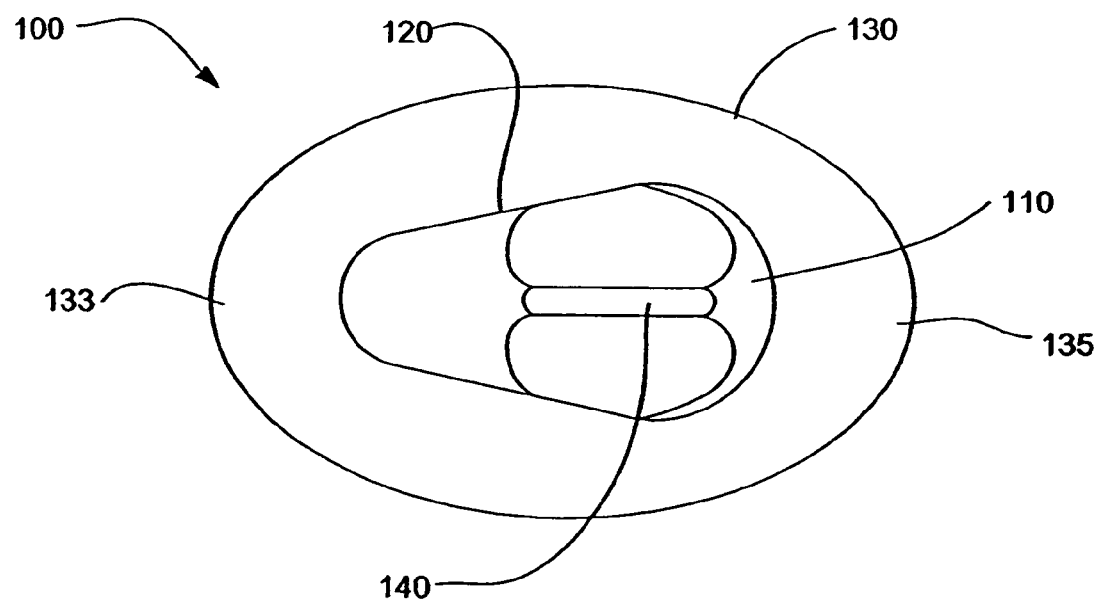
FIG. 2 is an end view of the implant of FIG. 1.

FIGS. 1 and 2 illustrate an implant 100 in accordance with an embodiment of the present invention. The implant 100 comprises a wing 130, a spacer 120, and a lead-in tissue expander (also referred to herein as a distraction guide) 110. The distraction guide 110 in this particular embodiment is wedge-shaped, i.e., the implant has an expanding cross-section from a distal end of the implant 102 to a region 104 where the guide 110 joins with the spacer 120 (referencing for the figures is based on the point of insertion of the implant between spinous processes). As such, the distraction guide functions to initiate distraction of the soft tissue and the spinous processes when the implant 100 is surgically inserted between the spinous processes. It is to be understood that the distraction guide 110 can be pointed and the like, in order to facilitate insertion of the implant 100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 1 and 2, there is no requirement to remove any of the bone of the spinous processes and no requirement to sever or remove from the body ligaments and tissues immediately associated with the spinous processes. For example, it is unnecessary to sever the ligamentum nuchae (supraspinous ligament), which partially cushions the spinous processes of the upper cervical vertebrae.

Figure 3:
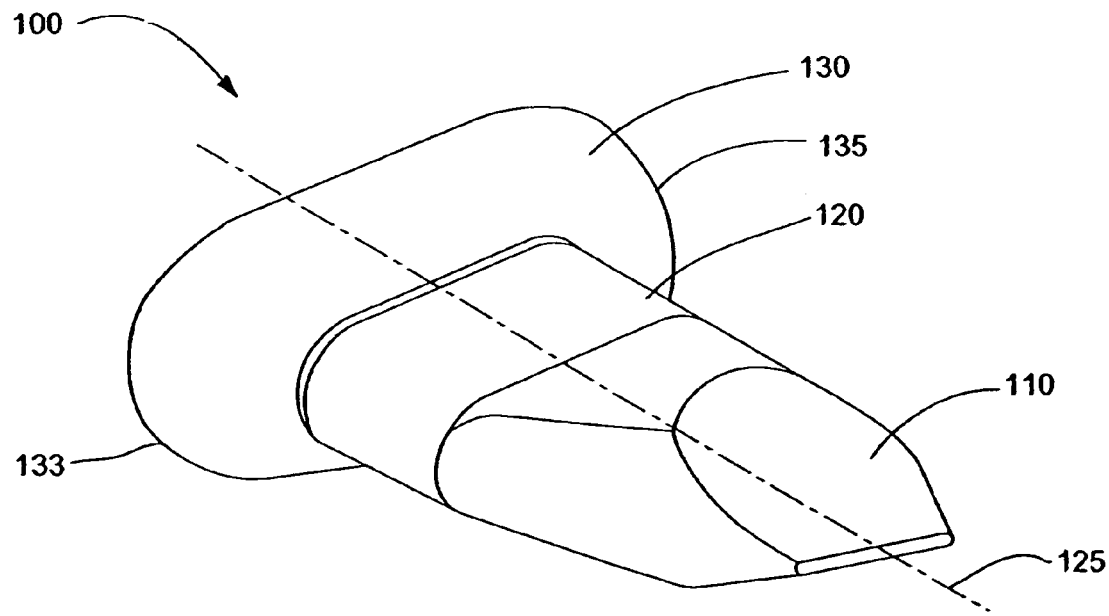
FIG. 3 is a perspective view of another embodiment of an implant in accordance with the present invention having a wing with a teardrop-shaped cross-section.

As can be seen in FIGS. 1-3, the spacer 120 can be teardrop-shaped in cross-section perpendicular to a longitudinal axis 125 of the implant 100. In this way, the shape of the spacer 120 can roughly conform to a wedge-shaped space, or a portion of the space, between adjacent spinous processes within which the implant 100 is to be positioned. In other embodiments, the spacer 120, can have alternative shapes such as circular, wedge, elliptical, ovoid, football-shaped, and rectangular-shaped with rounded corners and other shapes, and be within the spirit and scope of the invention. The shape of the spacer 120 can be selected for a particular patient so that the physician can position the implant 100 as close as possible to the anterior portion of the surface of the spinous process. The shape selected for the spacer 120 can affect the contact surface area of the implant 100 and the spinous processes that are to be subject to distraction. Increasing the contact surface area between the implant 100 and the spinous processes can distribute the force and load between the spinous frame and the implant 100.

As can be seen in FIGS. 1 and 2, the wing 130 in an embodiment can be elliptically shaped in cross-section perpendicular to the longitudinal axis 125. The dimensions of the wing 130 can be larger than that of the spacer 120, particularly along the axis of the spine, and can limit or block lateral displacement of the implant 100 in the direction of insertion along the longitudinal axis 125. As illustrated in the embodiment of FIG. 3, the wing 130 can alternatively have other cross-sectional shapes, such as teardrop, wedge, circular, ovoid, football-shaped, and rectangular-shaped with rounded corners and other shapes, and be within the spirit and scope of the invention. The wing 130 has an anterior portion 138 and a posterior portion 136.

In other embodiments, the implant 100 can include two wings, with a second wing 160 (shown in FIG. 4) separate from the distraction guide 110, spacer 120 and first wing 130. The second wing 160 can be connected to the distal end of the spacer 120. The second wing 160, similar to the first wing 130, can limit or block lateral displacement of the implant 100, however displacement is limited or blocked in the direction along the longitudinal axis 125 opposite insertion. When both the first wing 130 and the second wing 160 are connected with the implant 100 and the implant 100 is positioned between adjacent spinous processes, a portion of the spinous processes can be sandwiched between the first wing 130 and the second wing 160, limiting any displacement along the longitudinal axis 125.

Figure 4:
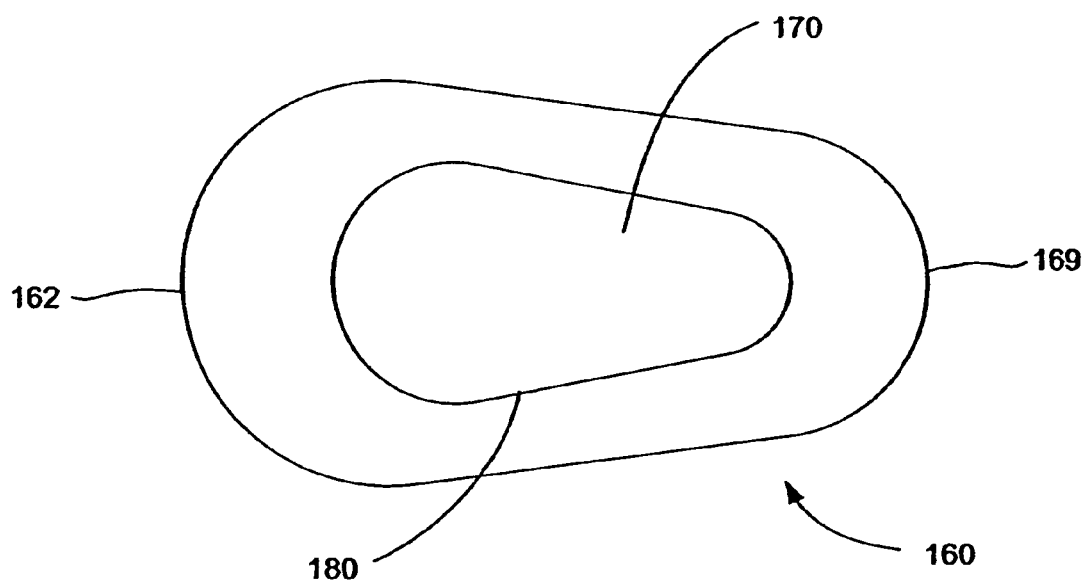
FIG. 4 is an end view of a second wing for use with the implant of FIG. 3.

As can be seen in FIG. 4, the second wing 160 can be teardrop-shaped in cross-section. The wider end 166 of the second wing 160 is the posterior end and the narrower end 168 of the second wing 160 is the anterior end. Unlike the first wing 130, however, an opening 164 is defined within the second wing 160, the opening 164 being at least partially circumscribed by a lip 162 that allows the second wing 160 to pass over the distraction guide 110 to meet and connect with the spacer 120. The second wing 160 can be secured to the spacer 120 once the second wing 160 is properly positioned. The second wing 160 can be connected with the implant after the implant 100 is positioned between the spinous processes.

It is to be understood that the implant can be made in two pieces. The first piece can include the first wing 130, the spacer 120, and the distraction guide 110. The second piece can include the second wing 160. Each piece can be manufactured using technique known in the art (e.g., machining, molding, extrusion). Each piece, as will be more fully discussed below, can be made of a material that is bio-compatible with the body of the patient. An implant can be formed with multiple pieces and with the pieces appropriately joined together, or alternatively, an implant can be formed as one piece or joined together as one piece.

Figure 5:
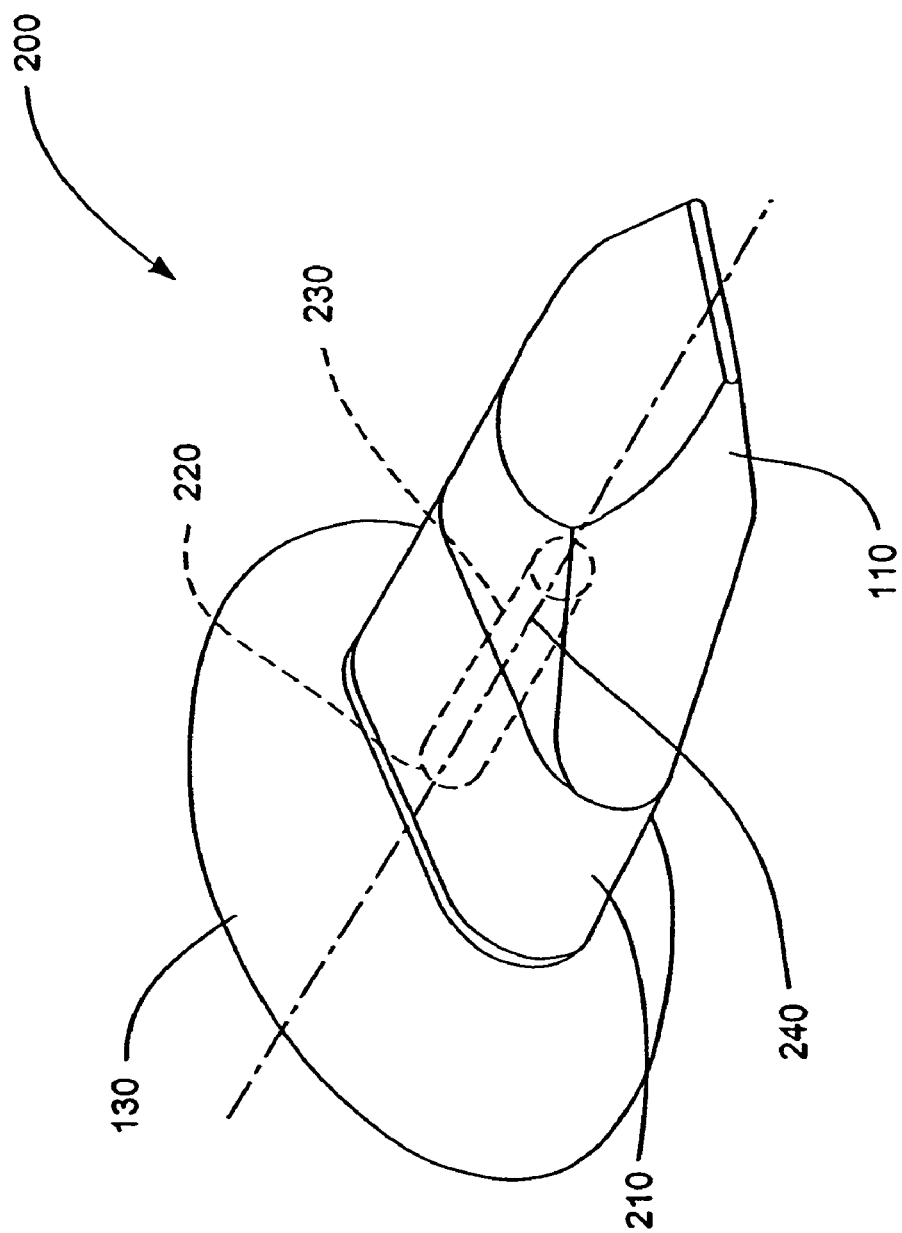
FIG. 5 is a perspective view of an embodiment of an implant in accordance with the present invention having a rotatable spacer and a wing with an elliptical cross-section.
Figure 6:
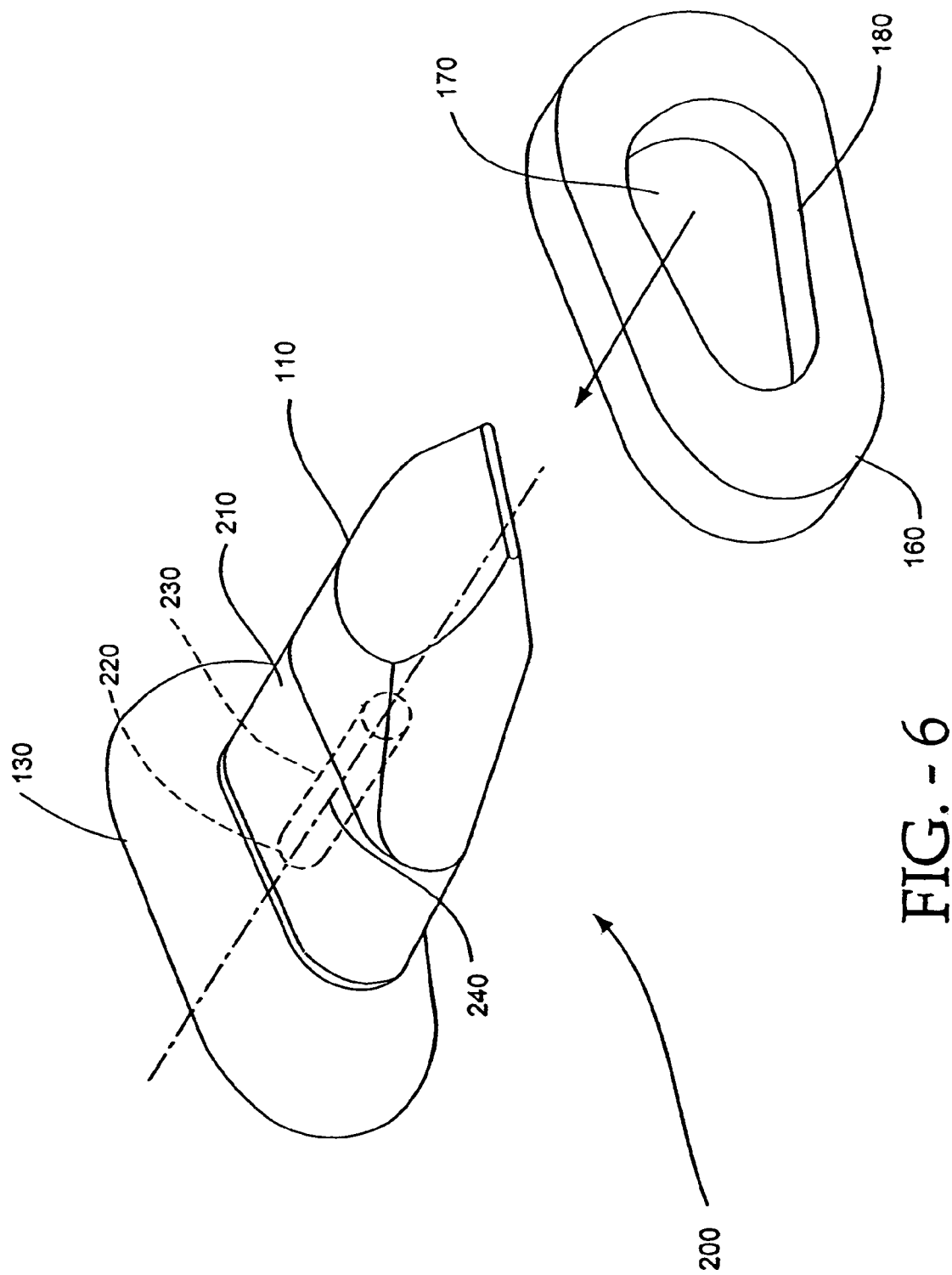
FIG. 6 is a perspective view of an embodiment of an implant in accordance with the present invention having a rotatable spacer with two wings that are teardrop-shaped in cross-section.
Figure 7:
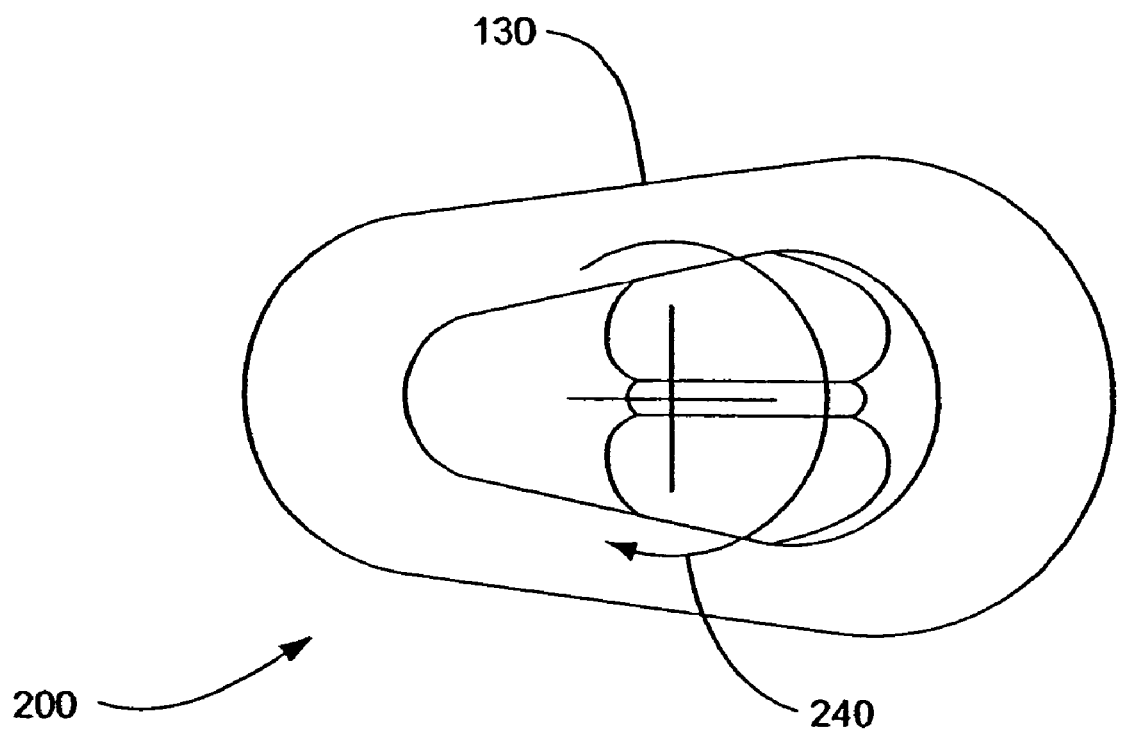
FIG. 7 depicts the axis of rotation of the implant of FIG. 6 as seen from an end view.

Further embodiments of implants in accordance with the present invention are depicted in FIGS. 5-7. In such embodiments, the spacer 220 can be rotatable about the longitudinal axis 225 relative to the first wing 130, or relative to the first wing 130 and a second wing 160 where two wings are used. The spacer 220 can be rotatable or fixed relative to the distraction guide 110. Where the spacer 220 is rotatable relative to the distraction guide 110, the spacer 220 can include a bore 222 running the length of the longitudinal axis 225, and a shaft 224 inserted through the bore 222 and connecting the distraction guide 110 with the first wing 130. It can be advantageous to position any of the implants taught herein as close as possible to the vertebral bodies. The rotatable spacer 220 can rotate to conform to or settle between adjacent spinous processes as the implant 200 is inserted and positioned during implantation, so that on average the contact surface area between the spacer 220 and the spinous processes can be increased over the contact surface area between a fixed spacer 120 and the spinous processes. Thus, the rotatable spacer 220 can improve the positioning of the spacer 220 independent of the wings 130,160 relative to the spinous processes. The embodiment of FIG. 6 includes a teardrop-shaped first wing 130, and a teardrop-shaped second wing 160, similar to the second wing 160 depicted in the embodiment of FIG. 3. As discussed below, the shape of the wings 130,160 in FIGS. 3 and 6 is such that the implants 100,200 accommodate the twisting of the cervical spine along its axis, for example, as the head of a patient turns from side to side.

Figure 8:
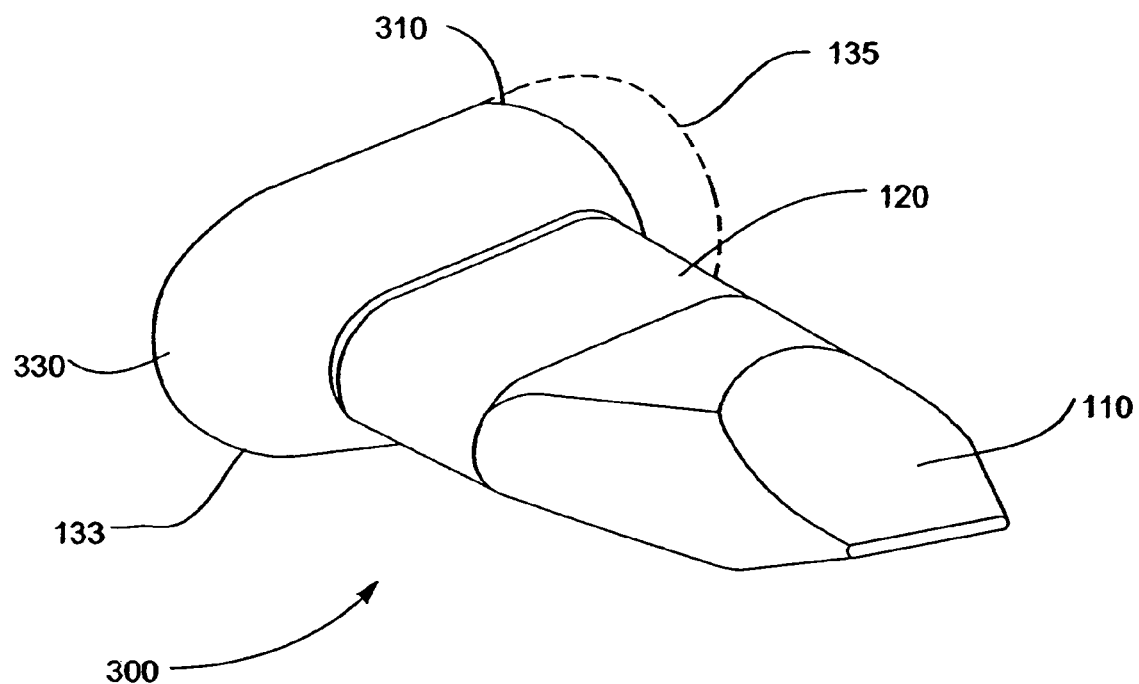
FIG. 8 is a perspective view of an embodiment of an implant in accordance with the present invention having a wing that is truncated at a posterior end.
Figure 9A:
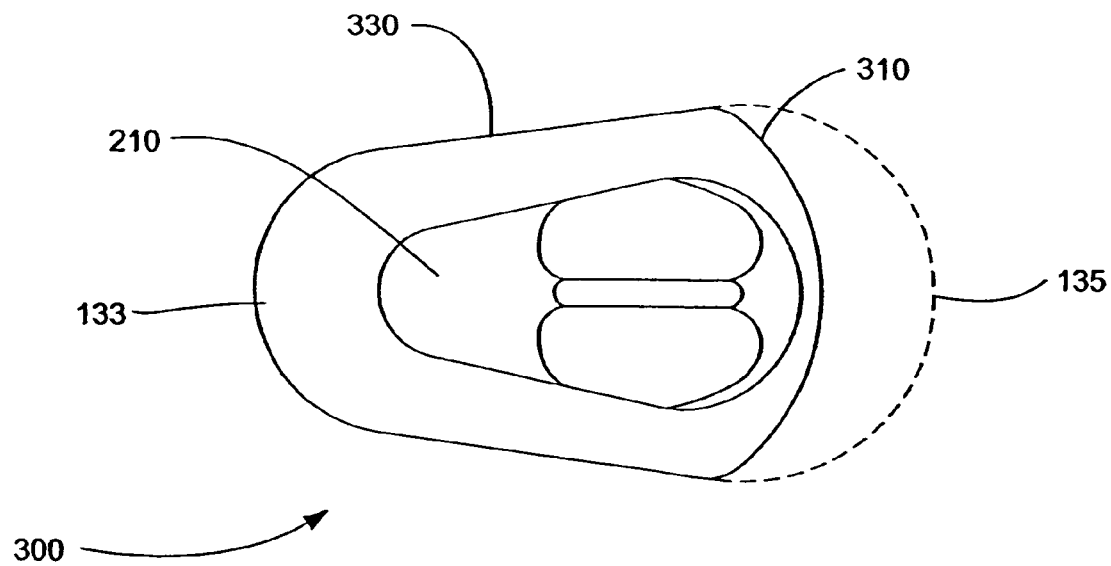
FIG. 9A is an end view of the implant of FIG. 8.
Figure 9B:
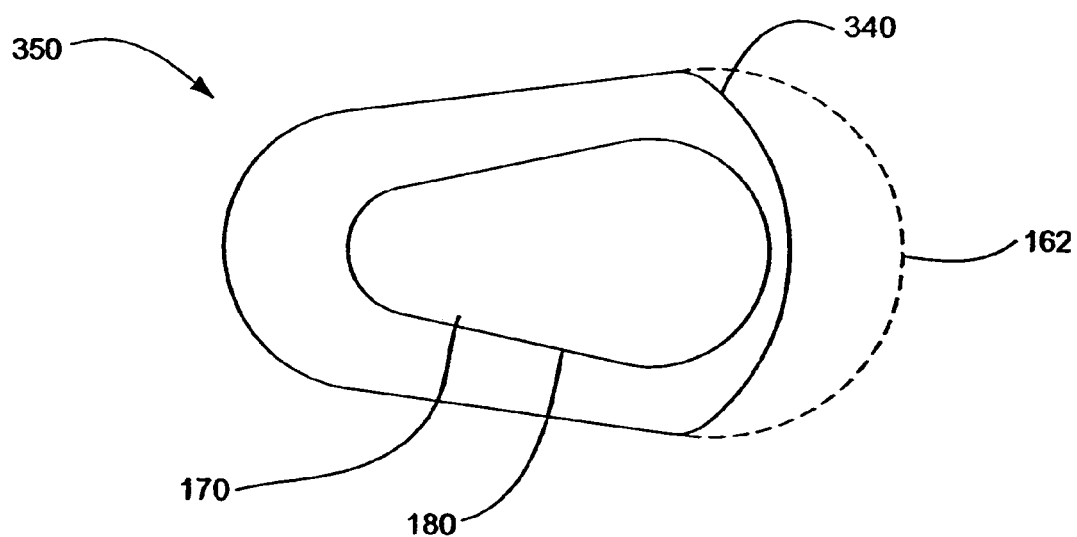
FIG. 9B is a truncated second wing for use with the implant of FIG. 9A.

FIG. 8 is a perspective view and FIG. 9A is an end view of still another embodiment of an implant in accordance with the present invention, wherein the posterior portion 336 of the teardrop-shaped first wing 330 is truncated, making the first wing 330 more ovoid in shape. In this configuration, the anterior portion 138 of the first wing 330 can be longer than the truncated posterior end 336 of the first wing 330. As in previous embodiments, the spacer 120 can alternatively be a rotatable spacer rather than a fixed spacer. FIG. 9B illustrates a second wing 360 for use with such implants 300, the second wing 360 having a truncated posterior end 366. Truncation of the posterior ends 336,366 of the first and second wings 330,360 can reduce the possibility of interference of implants 300 having such first and second wings 330,360 positioned between spinous processes of adjacent pairs of cervical vertebrae, e.g., implants between cervical vertebrae five and six, and between cervical vertebrae six and seven. During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

Figure 10:
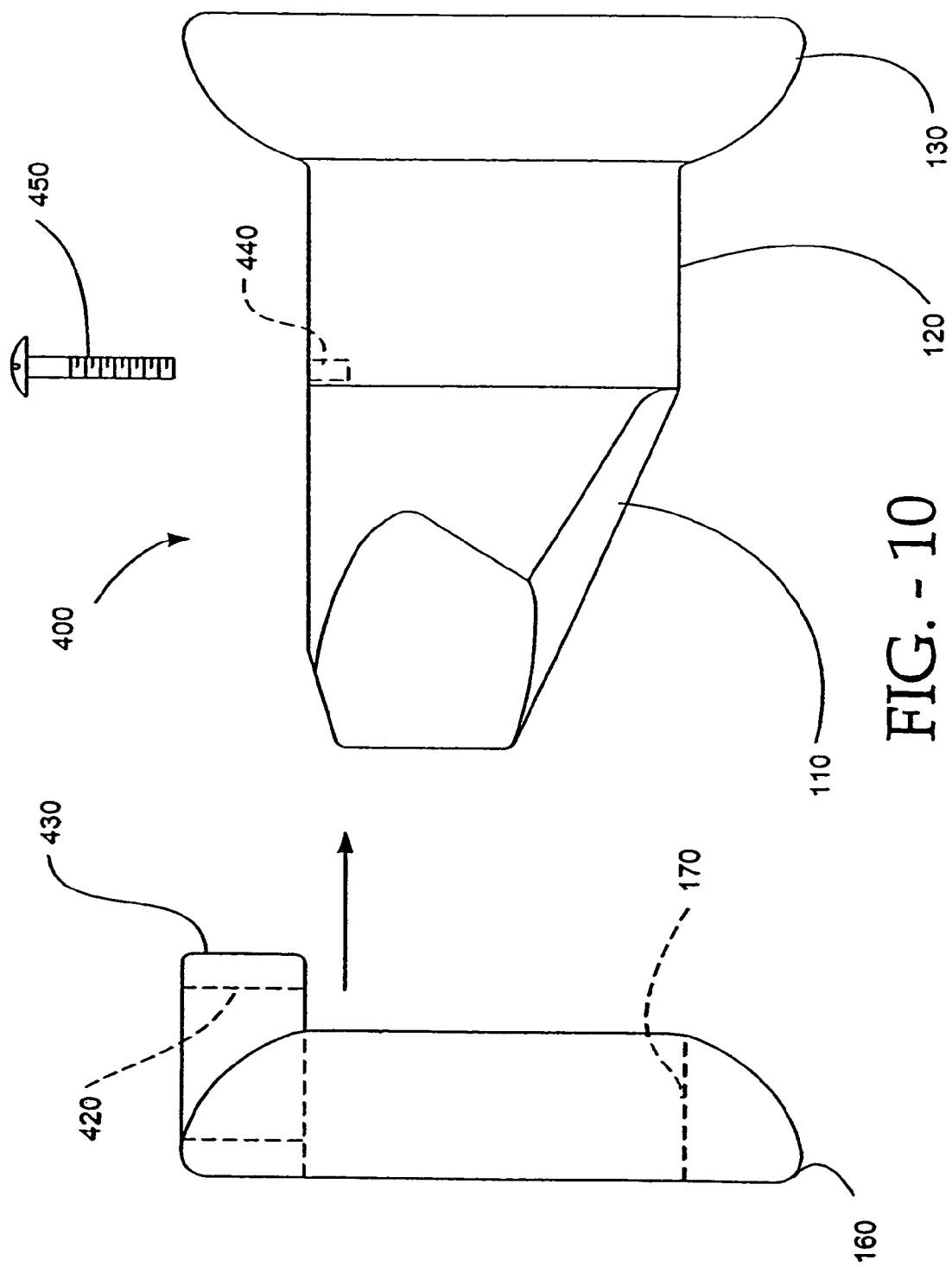
FIG. 10 is a plan view of an embodiment of an implant in accordance with the present invention wherein a screw is used to secure a second wing to the spacer.
Figure 11:
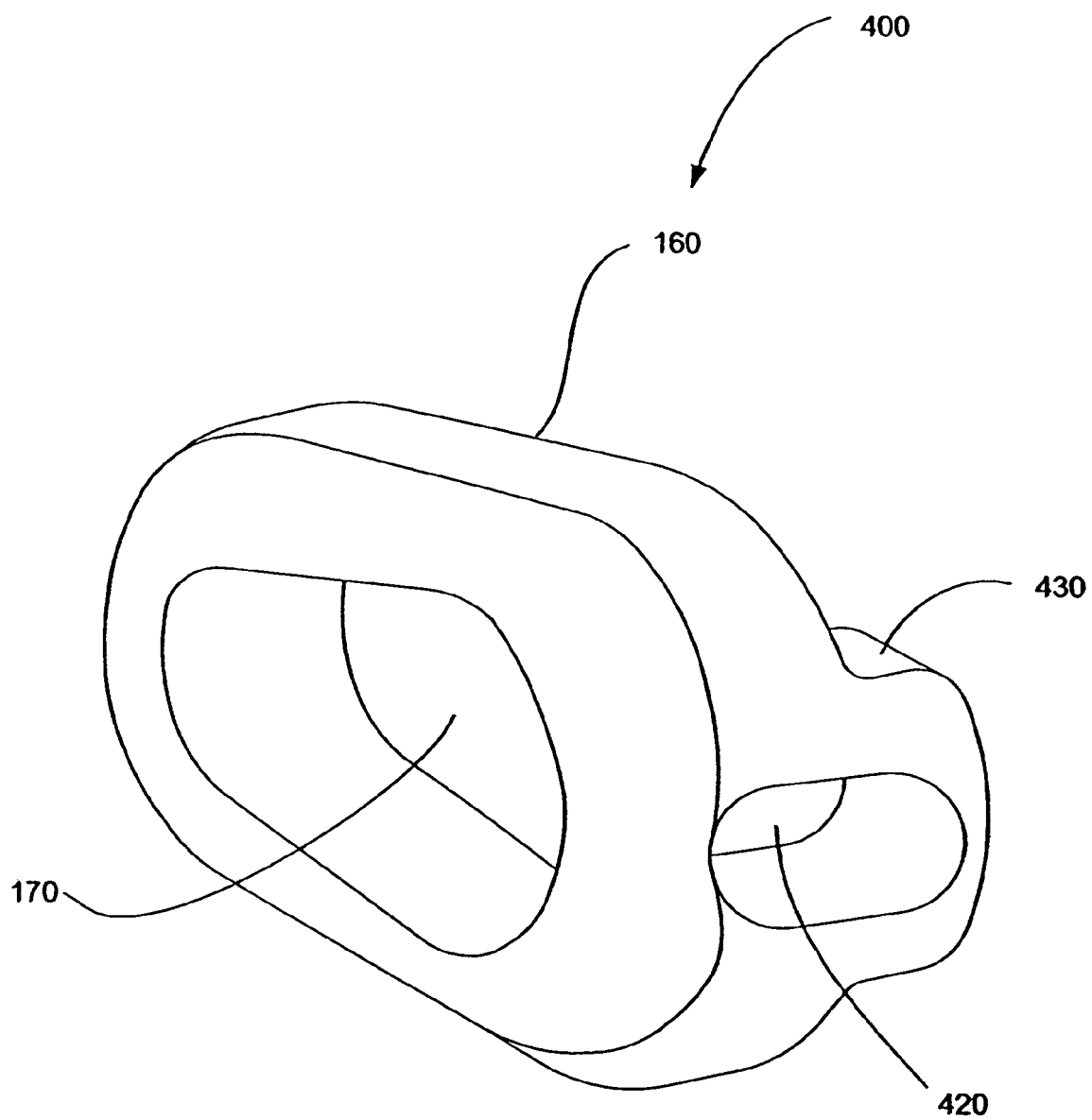
FIG. 11 is a perspective view of the second wing of FIG. 10.
Figure 12:
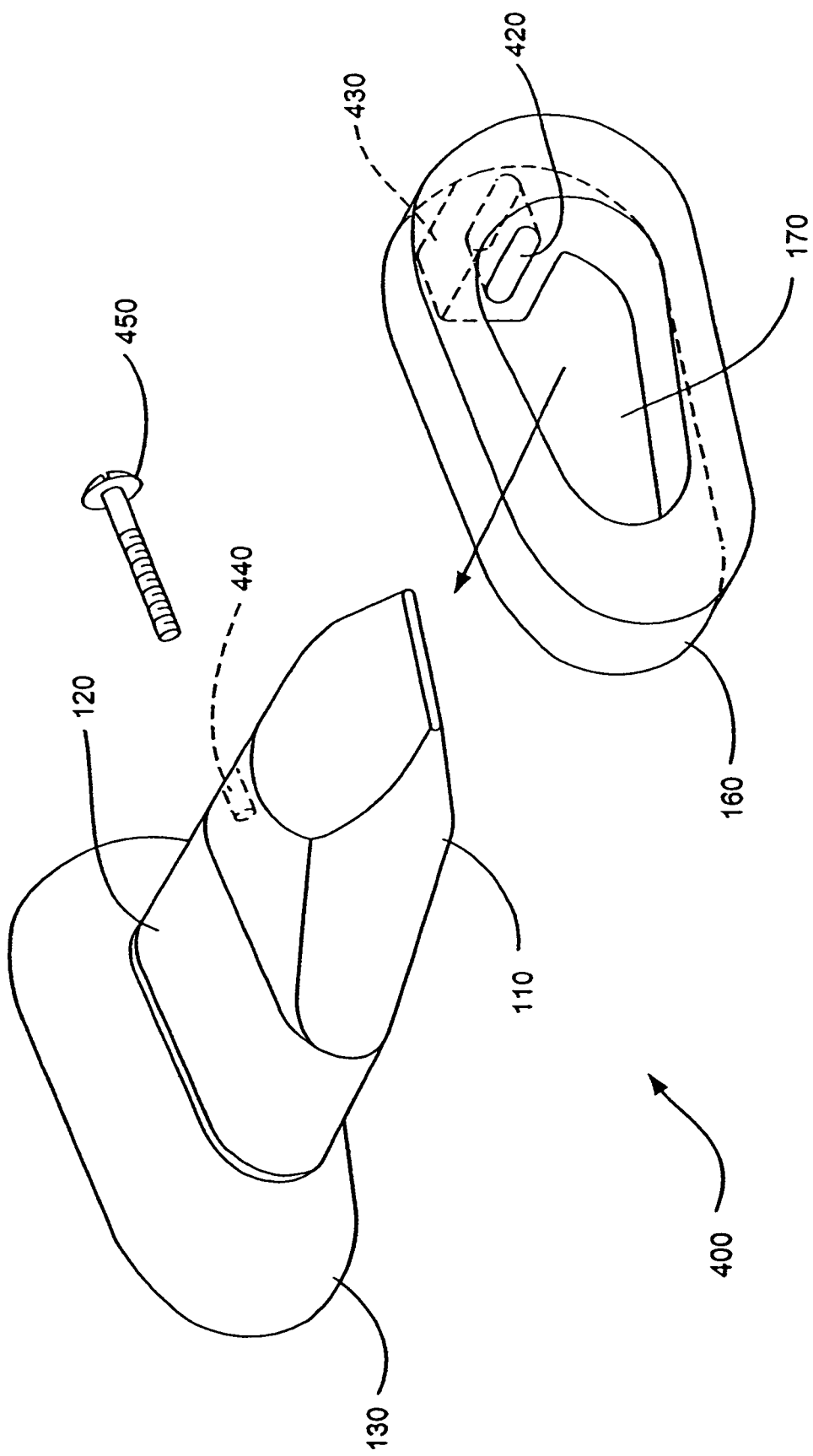
FIG. 12 is a perspective view of the implant of FIG. 10.
Figure 13A:
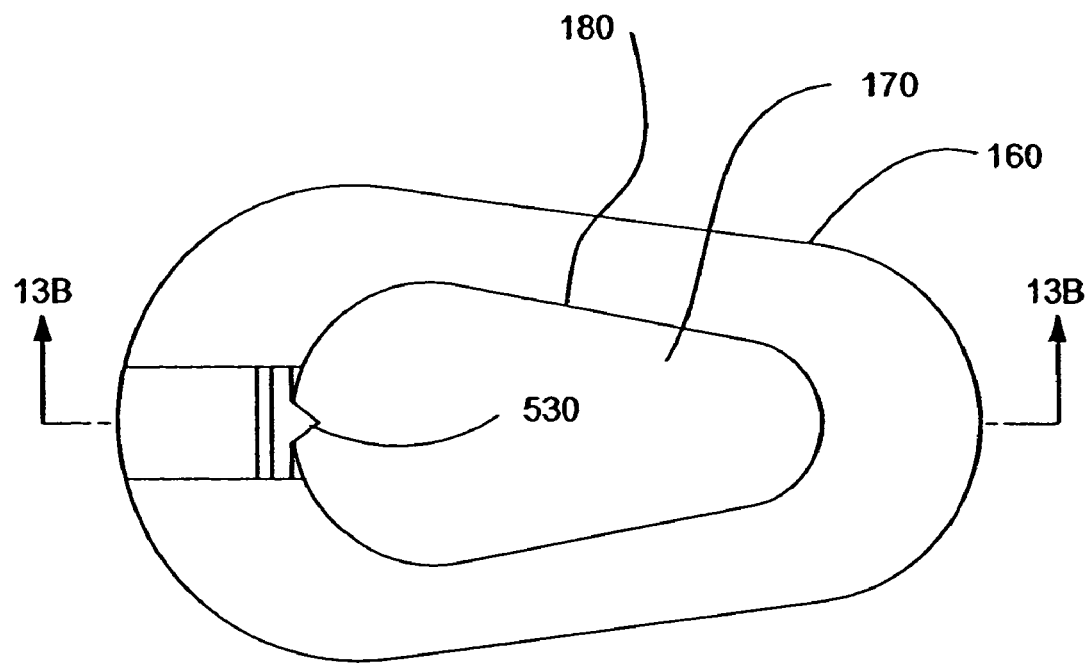
FIG. 13A is a front view of a second wing for use with some embodiments of implants of the present invention having a flexible hinge mechanism for securing the second wing to an implant.
Figure 13B:
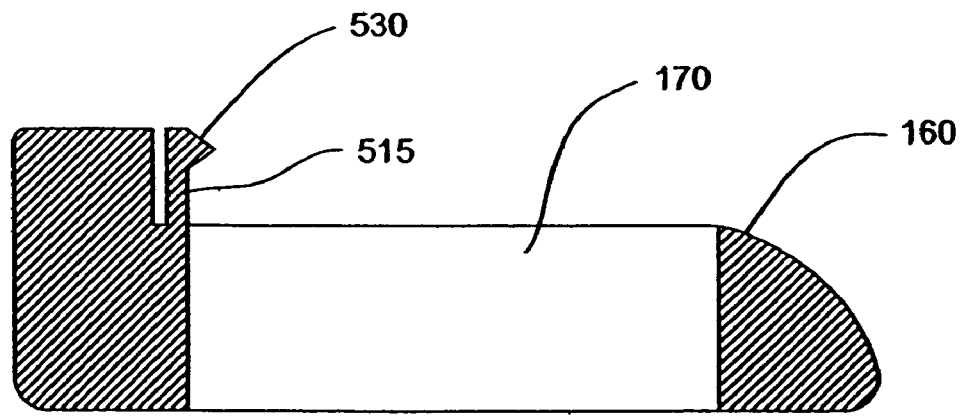
FIG. 13B is a side-sectional view of the second wing of FIG. 13A.
Figure 14A:
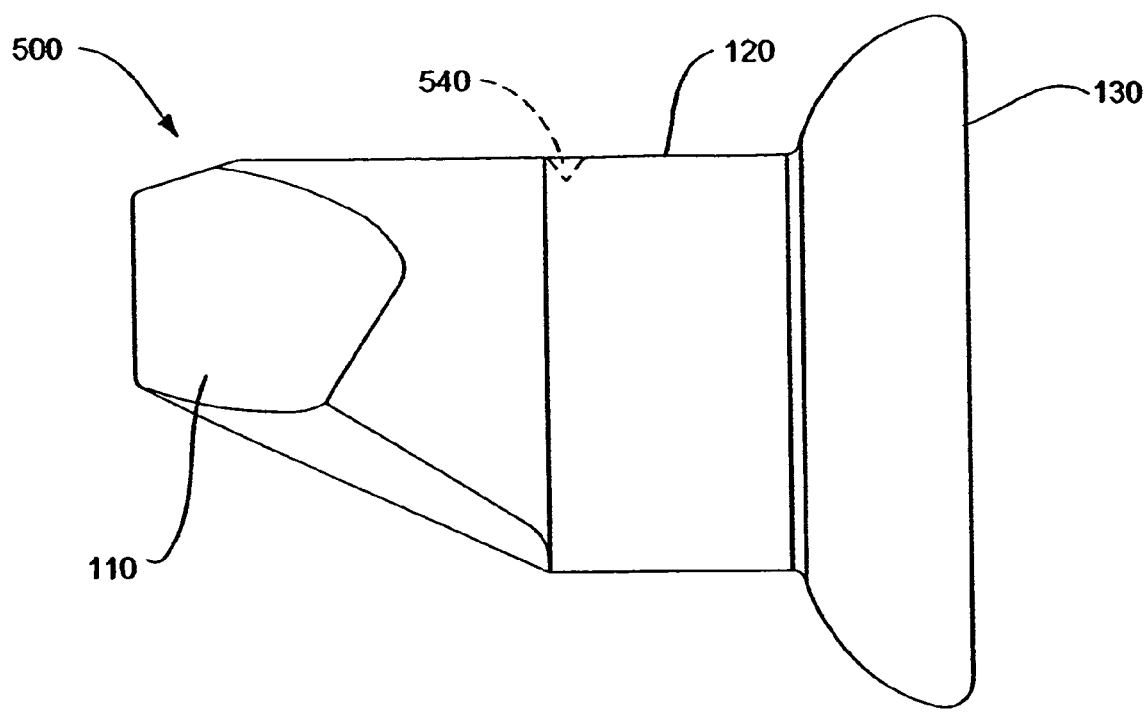
FIG. 14A is a plan view of an embodiment of an implant for use with the second wing of FIGS. 13A and 13B.
Figure 14B:
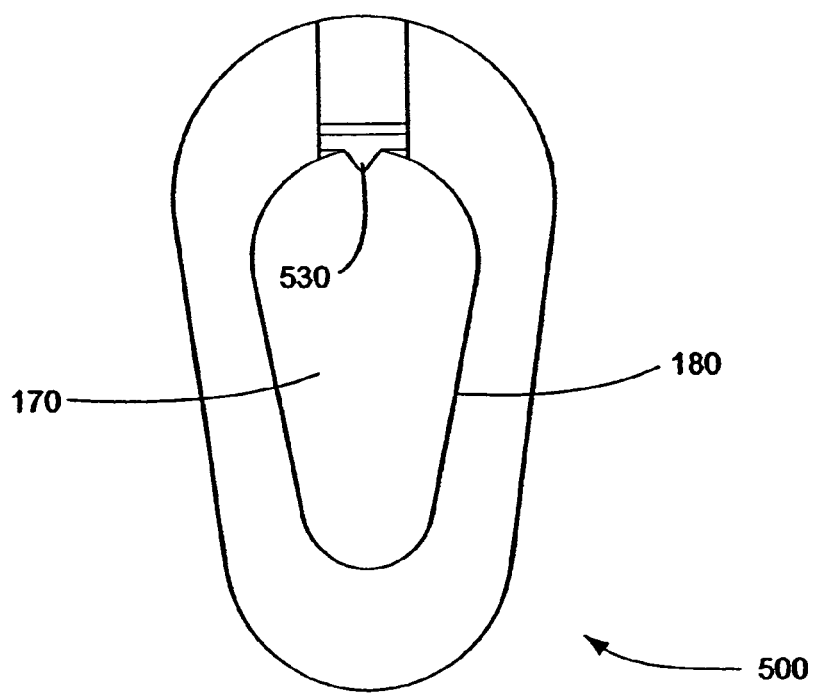
FIG. 14B is a front view of the second wing of FIGS. 13A and 13B.

With respect to the prior embodiments which have first and second wings 130,160, the second wing 160, can be designed to be interference-fit onto the spacer 120 (where the spacer is fixed) or a portion of the distraction guide 110 adjacent to the spacer 120 (where the spacer is rotatable). Where the second wing 160 is interference-fit, there is no additional attachment device to fasten the second wing 160 relative to the remainder of the implant. Alternatively, various fasteners can be used to secure the second wing relative to the remainder of the implant. For example, FIGS. 10-12 illustrate an embodiment of an implant 400 including a teardrop-shaped second wing 460 having a bore 463 through a tongue 461 at the posterior end of the second wing 460. The bore 463 is brought into alignment with a corresponding bore 440 on the spacer 120 when the second wing 460 is brought into position by surgical insertion relative to the rest of the implant 400. A threaded screw 442 can be inserted through the aligned bores 463,440 in a posterior-anterior direction to secure the second wing 460 to the spacer 120. The direction of insertion from a posterior to an anterior direction has the screw 442 engaging the bores 463,440 and the rest of the implant 400 along a direction that is generally perpendicular to the longitudinal axis 125. This orientation is most convenient when the surgeon is required to use a screw 442 to secure the second wing 460 to the rest of the implant 400. Other securing mechanisms using a member inserted into corresponding bores 463,440 on the spacer 120 and second wing 460 are within the spirit of the invention. It should be understood that a rotatable spacer 220 also can be accommodated by this embodiment. With a rotatable spacer 220, the second wing 460 would be attached to a portion of the distraction guide 110 that is located adjacent to the rotatable spacer 220.

FIGS. 13A-14B depict a further embodiment 500 wherein the second wing 560 is secured to the spacer 120 by a mechanism including a flexible hinge 565, with a protrusion 561 on the end of the hinge 565 adjacent to the lip 562 of the opening 564 defined by portions of the second wing 560. The securing mechanism also encompasses an indentation 540 on the spacer 120, wherein the indentation 540 accommodates the protrusion 561 on the end of the flexible hinge 565. During surgery, after insertion of the distraction guide 110, spacer 120, and first wing 130, the second wing 560 is received over the distraction guide 110 and the spacer 120. As the second wing 560 is received by the spacer 120, the flexible hinge 565 and its protrusion 561 deflect until the protrusion 561 meets and joins with the indentation 540 in the spacer 120, securing the second wing 560 to the spacer 120. Again in embodiments where the spacer can rotate, the indentation 540 is located on an end of the distraction guide 110 that is adjacent to the rotatable spacer 220. With respect to the flexible hinge 565, this hinge is in a preferred embodiment formed with the second wing 560 and designed in such a way that it can flex as the hinge 565 is urged over the distraction guide 110 and the spacer 120 and then allow the protrusion 561 to be deposited into the indentation 540. Alternatively, it can be appreciated that the indentation 540 can exist in the second wing 560 and the flexible hinge 565 and the protrusion 561 can exist on the spacer 120 in order to mate the second wing 560 to the spacer 120. Still alternatively, the flexible hinge 565 can be replaced with a flexible protrusion that can be flexed into engagement with the indentation 540 in the embodiment with the indentation 540 in the spacer 120 or in the embodiment with the indentation 540 in the second wing 560. One of ordinary skill in the art will appreciate the myriad different ways with which the second wing can be mated with the implant.

Figure 15A:
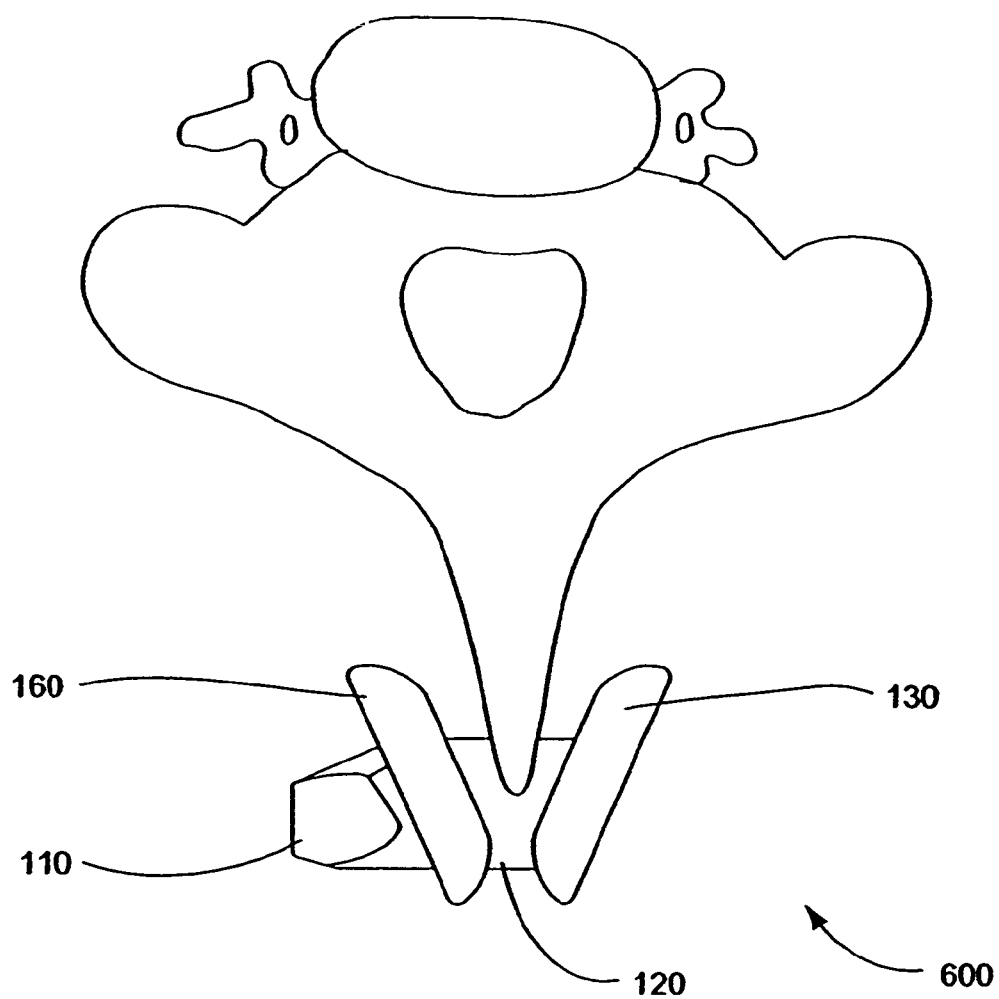
FIG. 15A is a top view of an embodiment of an implant in accordance with the present invention positioned between spinous processes of adjacent cervical vertebrae.
Figure 15B:
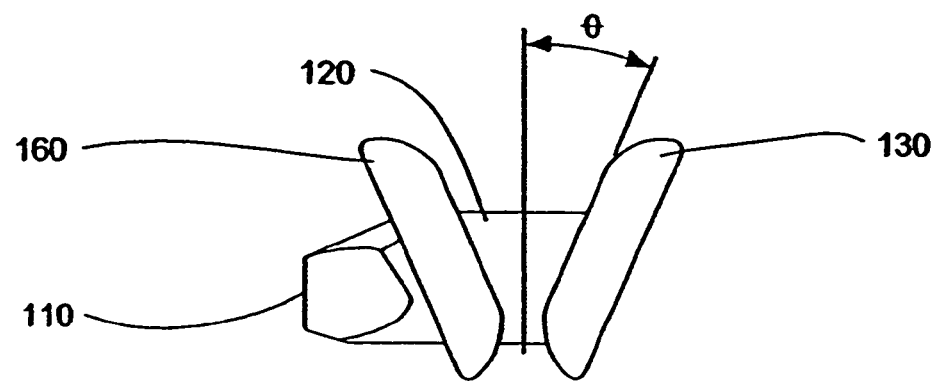
FIG. 15B is a top view of the implant of FIG. 15A showing wing orientation.
Figure 16:
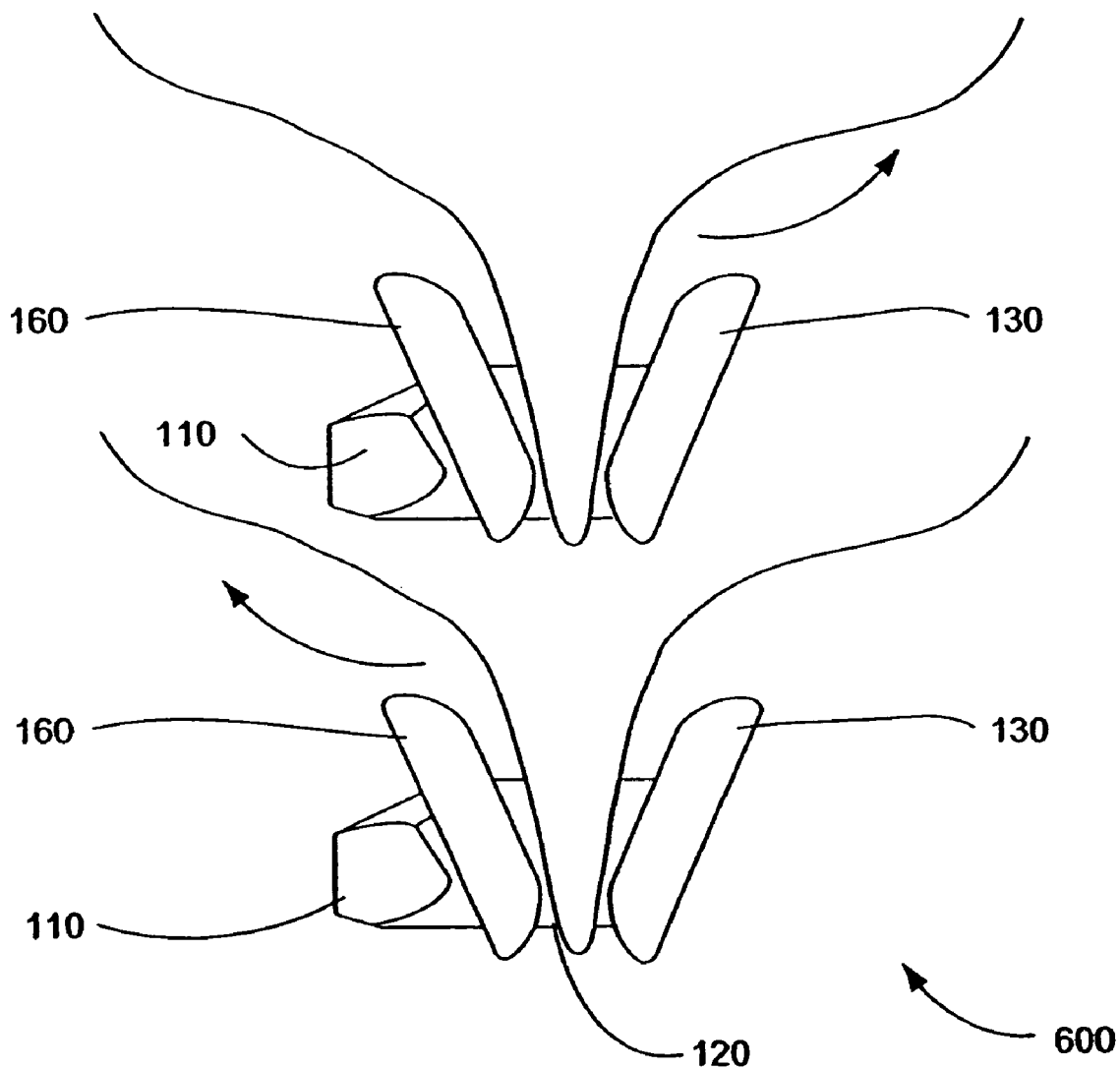
FIG. 16 is a top view of two such implants of the invention of FIG. 15A and 15B, positioned in the cervical spine.

FIGS. 15A-16 illustrate an embodiment of an implant 600 wherein anterior ends of a first wing 630 and second wing 660 flare out at an angle away from the spacer 120 and away from each other. The cervical spinous processes are themselves wedge-shaped when seen from a top view. The first wing 630 and second wing 660 flare out so that the implant 600 can roughly conform with the wedge shape of the spinous processes, allowing the implant 600 to be positioned as close as possible to the vertebral bodies of the spine where the load of the spine is carried. The first and second wings 630,660 are positioned relative to the spacer, whether the spacer is fixed 120 or rotatable 220, so that the wings flare out as the wings approach the vertebral body of the spine. FIG. 15B is a top view of the implant 600 of FIG. 15A removed from proximity with the spinous processes. The first wing 630 is aligned at an angle with respect to an axis along the spinous processes perpendicular to the longitudinal axis (also referred to herein as the plane of symmetry). In one embodiment, the angle is about 30°, however, the angle θ can range from about 15° to about 45°. In other embodiments, other angles outside of this range are contemplated and in accordance with the invention. Likewise, the second wing 660 can be aligned along a similar, but oppositely varying range of angles relative to the plane of symmetry.

As described above in reference to FIG. 4, the second wing 660 defines an opening which is outlined by a lip. As is evident, the lip can be provided at an angle relative to the rest of the second wing 660 so that when the lip is urged into contact with the spacer 120, the second wing 660 has the desired angle relative to the spacer 120. As discussed above, there are various ways that the second wing 660 is secured to the spacer 120. FIG. 15A depicts a top view of one such implant 600 placed between the spinous processes of adjacent cervical vertebrae. FIG. 16 is a top view illustrating two layers of distracting implants 600 with flared wings 630,660.

Figure 17:
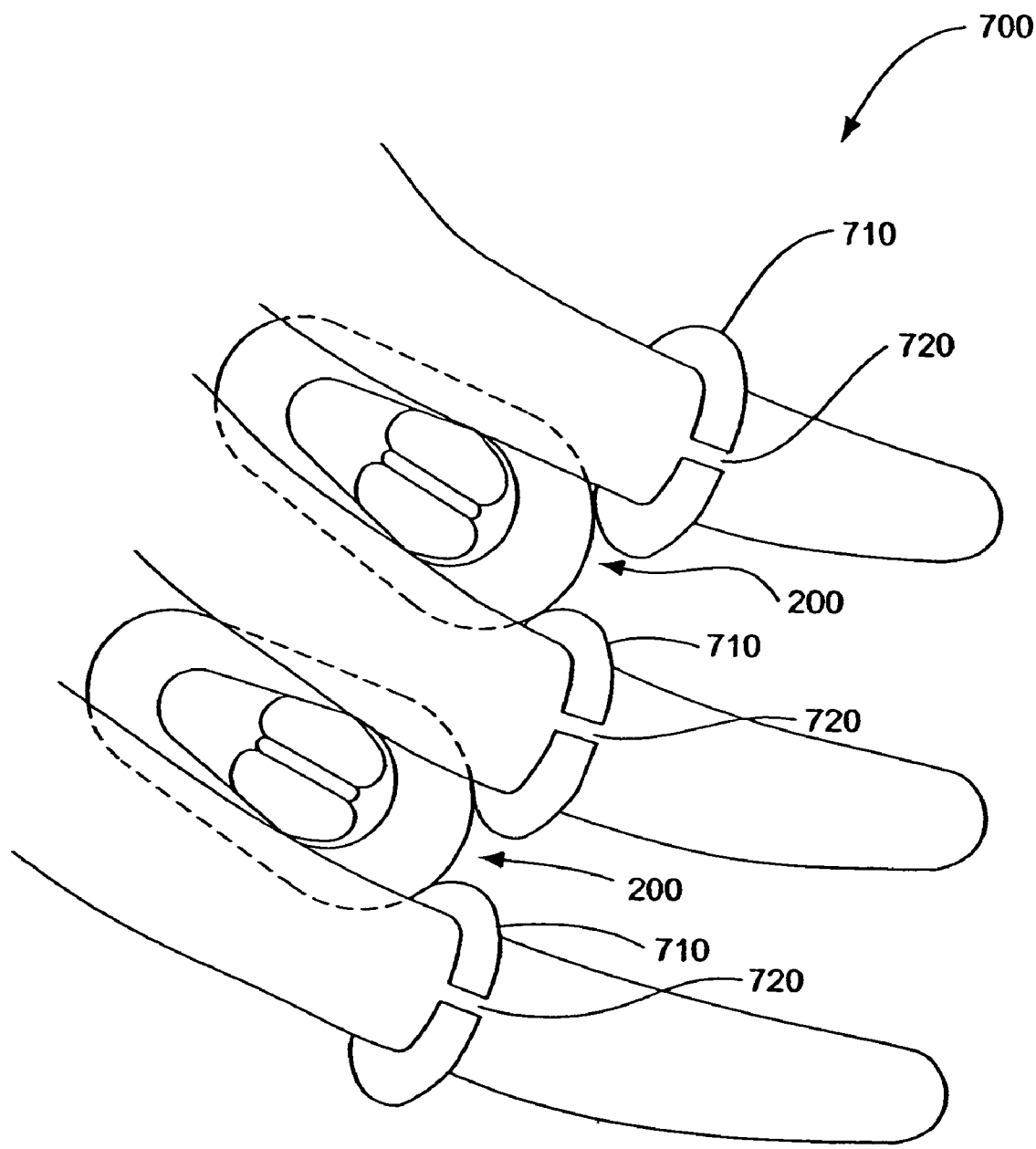
FIG. 17 is a side view of two implants of the invention positioned in the cervical spine, with stops or keeps at the proximal ends of the spinous processes.

Systems and methods in accordance with the present invention can include devices that can be used in cooperation with implants of the present invention. FIG. 17 illustrates "stops" (also referred to herein as "keeps") 656, which are rings of flexible biocompatible material, which can be positioned around the spinous processes of adjacent cervical vertebrae and located posteriorly to the implant 600. The keeps 656 can prevent posterior displacement of implants. In one embodiment, the keeps can include a ring having a slit 658. The keeps 656 can be somewhat sprung apart, so that the keep 656 can be fit over the end of the spinous process and then allowed to spring back together in order to hold a position on the spinous process. The keep 656 can act as a block to the spacer 120 in order to prevent the implant 600 from movement in a posterior direction.

Interspinous Implant having Slide-In Distraction Piece

Figure 18A:
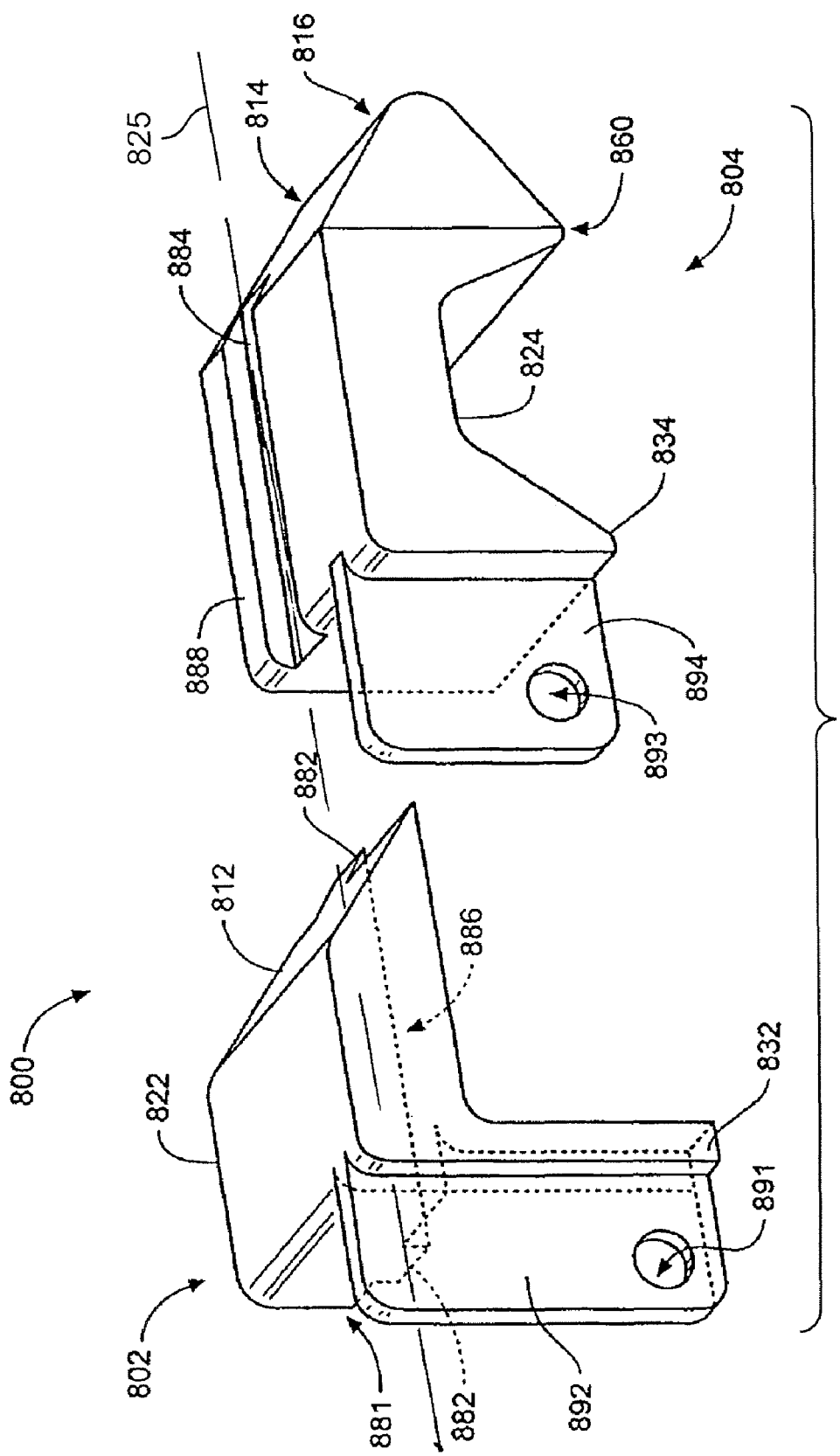
FIG. 18A is a perspective view of an alternative embodiment of an implant for use with systems and methods of the present invention, the implant including an distraction piece mated with a initiating piece.
Figure 18:
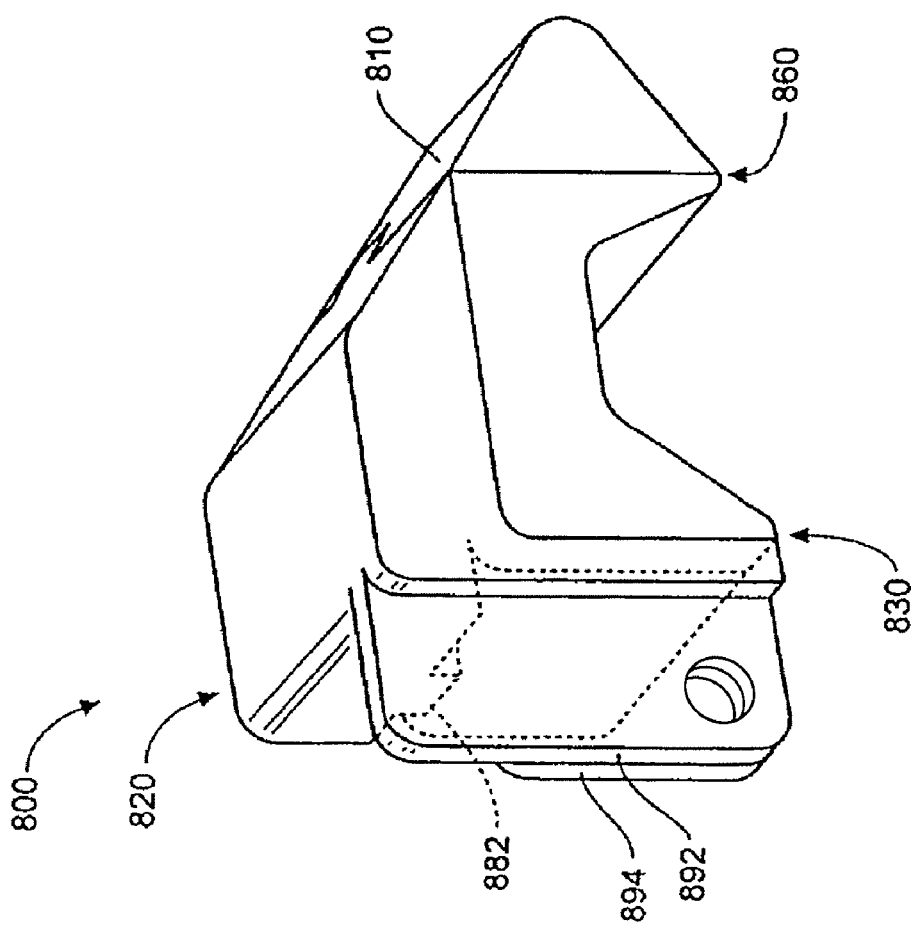
FIG. 18B is a perspective view of the implant of FIG. 18A, the implant including an distraction piece mated with a initiating piece.

FIGS. 18A and 18B are perspective end views of an alternative embodiment of an implant 800 in accordance with the present invention. The implant 800 can include an initiating piece 804 and a slide-in distraction piece 802 that can be slidably coupled with the initiating piece 804. The initiating piece 804 and the slide-in distraction piece 802, when positioned between adjacent spinous processes and coupled together as shown in FIG. 18B, has a saddle shape including a first wing 830 and a second wing 860 that straddle one of the adjacent spinous processes. The implant 800 approximates implants as shown above in FIGS. 1-17. For example, the implant 800 includes the first wing 830 at a proximal end of the implant 800, a fixed spacer 820 extending from the first wing 830, the second wing 860 extending from the spacer 820 so that the spacer 820 is disposed between the first wing 830 and the second wing 860, and a distraction guide 810 at a distal end 816 of the implant 800.

The initiating piece 804 includes a slot 884 within a lower sliding surface 888 that extends through a substantial portion of the length of the initiating piece 804, the slot 884 being adapted to receive a rail 882 of the slide-in distraction piece 802. The slot 884 can optionally include a flange or some other structure to retain the rail 882 within the slot 884. One of the slot 884 and the rail 882 can further optionally include a recess (not shown) adapted to receive a catch (not shown) of the other of the slot 884 and the rail 882 so that when the catch passes over the recess, the catch is extended, locking the distraction piece 802 in place, and limiting or blocking movement along the longitudinal axis 825.

As shown, the initiating piece 804 includes a first tab 894 extending from the first wing 834, the first tab 894 including a first perforation 893. The distraction piece 802 likewise includes a second tab 892 including a second perforation 891 adapted to be aligned with the first perforation 893 so that when the slide-in distraction piece 802 is mated with the initiating piece 804 and the rail 882 is seated within the slot 884, the first perforation 893 and the second perforation 891 are aligned and can be pegged together so that relative movement between the distraction piece 802 and the initiating piece 804 is limited or substantially blocked. In other embodiments, the initiating piece 804 and distraction piece 802 need not include tabs 892,894, for example where a catch and recess of the slot and rail is employed. Further, where a first tab 894 or other structure protrudes from the initiating piece 804, the distraction piece 802 can include a slot for receiving the tab 894, rather than a second tab 892 abutting the first tab 894. As will be obvious to one of ordinary skill in the art, tabs having myriad different shapes and sizes can extend from one or both of the initiating piece 804 and the distraction piece 802, and perforations having myriad different shapes and sizes can be formed within such tabs to limit relative movement between the initiating piece 804 and the distraction piece 802. Further, myriad different locking mechanisms (e.g., a tab and slot arrangement) can be employed with one or both of the initiating pieces 804 and the distraction piece 802 to limit relative movement. Embodiments of implants 800 in accordance with the present invention are not intended to be limited to those arrangements shown in FIGS. 18A-19E.

The initiating piece 804 includes a lower distraction element 814 having a contact surface that tapers to the distal end 816 from above as well as below the distal end 816 so that the lower distraction element 814 has a "V" shape in cross-section along an axis of the spine. The initiating piece 804 further includes a first portion 834 of the first wing, the second wing 860, and a lower portion 824 of the spacer. In an embodiment, the portions 824,834 and the second wing 860 can be integrally formed with the lower distraction element 814, thereby avoiding discontinuities in a lower sliding surface 888 of the initiating piece 804. A relatively continuous sliding surface 888 with smooth transitions improves ease of implantation and minifies obstruction of the initiating piece 804 by the adjacent spinous processes and/or related tissues. It is preferable that the initiating piece 804 include smooth transitions between the lower distraction element 814, the second wing 860, and the lower portion 824 of the spacer, as such transitions can increase obstruction of implant movement during implantation. The lower sliding surface 888 of the initiating piece 804 is substantially flat and preferably smooth to ease receipt of the rail 882 within the slot 884.

As described above, the slide-in distraction piece 802 includes the rail 882 extending over a substantial portion of the length of the distraction piece 802, roughly corresponding to a length of the slot 884 of the initiating piece 804 within which the rail 882 is adapted to be received. The height of the rail 882 from the upper sliding surface 886 approximately corresponds to the depth of the slot 884 so that when the rail 882 is received within the slot 884, the upper sliding surface 886 of the distraction piece 802 is substantially flush with the lower sliding surface 888. In other embodiments, a gap can exist between the upper sliding surface 886 and the lower sliding surface 888. As described above, the surface of the rail 882 can include a catch (or a recess) arranged along the length of the rail 882 so that the catch (or recess) roughly corresponds to the recess (or catch) disposed within the slot 884. In other embodiments, the rail 882 and slot 884 need not include a catch and recess arrangement, but rather the initiating piece 804 and the distraction piece 802 can be held in relative position along the longitudinal axis 825 when the first and second holes 891,893 are pegged together. In still other embodiments, some other mechanism can be used to limit or block relative movement of the initiating piece 804 and the distraction piece 802.

The distraction piece 802 further includes an upper distraction element 812, a second portion 832 of the first wing and an upper portion 822 of the spacer. The upper distraction element 812 has a contact surface that tapers at a distal end of the distraction piece 802 so that the upper distraction element 812 has a ramp shape. The second portion 832 of the first wing can have a shape that roughly conforms to the shape of the first portion 834 of the first wing so that when the distraction piece 802 is coupled to the initiating piece 804, the first and second portions 832,834 form a first wing 830, as shown in FIG. 18B. The upper portion 822 of the spacer can have a thickness greater or less than that of the lower portion 824 of the spacer. As shown, the upper portion 822 is thicker than the lower portion 824. By minifying the thickness of the lower portion 824, distraction of the adjacent spinous processes during implantation of the initiation piece 804 can be minified to cause less distraction at the surgical site by the second wing 860 as the second wing 860 is urged between the adjacent spinous processes. Alternatively, a plurality of distraction pieces 802 can be provided each having an upper portion 822 of the spacer having a different thickness. Thus the doctor can select the appropriate distraction piece 802 for the amount of distraction desired. As with the lower sliding surface 888, the upper sliding surface 886 of the distraction piece 802 is substantially flat and preferably smooth to ease positioning of the rail 882 within the slot 884. Embodiments of systems in accordance with the present invention can include a initiating piece 804 and a plurality of distraction pieces 802, the distraction pieces 802 having a variety of thicknesses. In such a system, a distraction piece 802 can be chosen so that the overall spacer 820 thickness is suitable for the patient and the motion segment targeted.

FIG. 19A is a posterior view of the initiating piece 804 positioned adjacent to the interspinous ligament 6. As can be seen, the initiating piece 804 has a maximum thickness from the lower sliding surface 888 to the second wing 860. As the initiating piece 804 is urged into the interspinous ligament 6, the lower distraction element 814 pierces and/or distracts the fibers of the interspinous ligament 6. As shown in FIG. 19B, the initiating piece 804 is further urged through the interspinous ligament 6 so that the second wing 860 passes between the adjacent spinous processes 2,4 and can distract the space between the adjacent spinous processes 2,4 to accommodate the second wing 860. The distraction of the space between the adjacent spinous processes is reduced by positioning the initiating piece 804 prior to coupling the distraction piece 802 to the initiating piece 804. Referring to FIG. 19C, the initiating piece 804 is further urged through the interspinous ligament 6 so that the lower portion 824 of the spacer is positioned between the adjacent spinous processes 2,4. The second wing 860 and the first portion 834 of the first wing straddle the lower spinous process 4. Once the initiating piece 804 is properly positioned, the rail 882 of the distracting piece 802 can be positioned within the proximal end of the slot 884, as shown in FIG. 19D. The distraction piece 804 can then be urged along the lower sliding surface 888 so that the upper distraction element 812 distracts the space between the adjacent spinous processes. As shown in FIG. 19E, the initiating piece 804 is further urged along the lower sliding surface 888 until the distraction piece 802 is mated with the initiating piece 804.

Materials For Use In Implants Of The Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

It is to be understood that embodiments in accordance with the present invention can be constructed without a pliant material. It is also to be understood that the embodiments in accordance with the present invention can have other dimensions.

Methods for Implanting Interspinous Implants

Figure 20A:
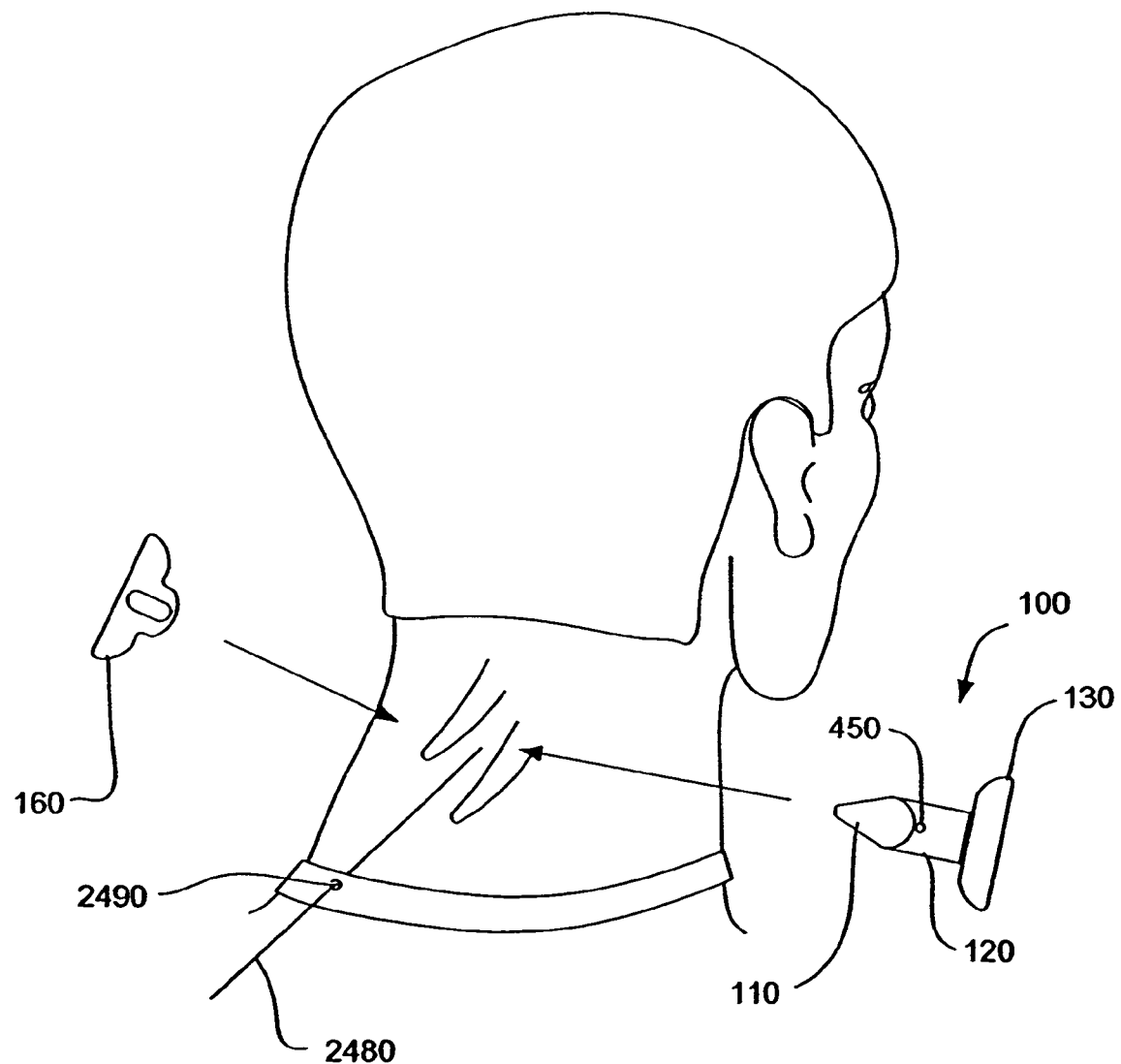
FIG. 20A illustrates an embodiment of a method in accordance with the present invention for implanting the interspinous implant of FIGS. 1-17.

A minimally invasive surgical method for implanting an implant 400 in the cervical spine is disclosed and taught herein. In this method, as shown in FIG. 20A, preferably a guide wire 80 is inserted through a placement network or guide 90 into the neck of the implant recipient. The guide wire 80 is used to locate where the implant is to be placed relative to the cervical spine, including the spinous processes. Once the guide wire 80 is positioned with the aid of imaging techniques, an incision is made on the side of the neck so that an implant in accordance with an embodiment of the present invention, can be positioned in the neck thorough an incision and along a line that is about perpendicular to the guide wire 80 and directed at the end of the guide wire 80. In one embodiment, the implant can be a sized implant 400 (i.e., having a body that is not distractable), such as described above in FIGS. 1-17 and including a distraction guide 110, a spacer 120, and a first wing 130. The implant 400 is inserted into the neck of the patient. Preferably during insertion, the distraction guide 110 pierces or separates the tissue without severing the tissue.

Once the implant 400 is satisfactorily positioned, a second wing 460 can be optionally inserted along a line that is generally colinear with the line over which the implant 400 is inserted but from the opposite side of the neck. The anatomy of the neck is such that it is most convenient and minimally invasive to enter the neck from the side with respect to the implant 400 and the second wing 460. The second wing 460 is mated to the implant and in this particular embodiment, the second wing 460 is attached to the implant 400 by the use of a fastener, for example by a screw 442. Where a screw is used, the screw 442 can be positioned using a screw driving mechanism that is directed along a posterior to anterior line somewhat parallel to the guide wire 80. This posterior to anterior line aids the physician in viewing and securing the second wing 460 to the implant. The second wing 460 is positioned so that a bore 463 formed in a lip 461 of the second wing 460 is aligned with a bore 440 of the implant 400, as described above. The screw 442 is positioned within both bores and secured, at least, to the bore 440 of the implant 400. In other embodiments, the second wing can be interference fit with the implant, as described above, or fastened using some other mechanism, such as a flexible hinge and protrusion.

Figure 20B:
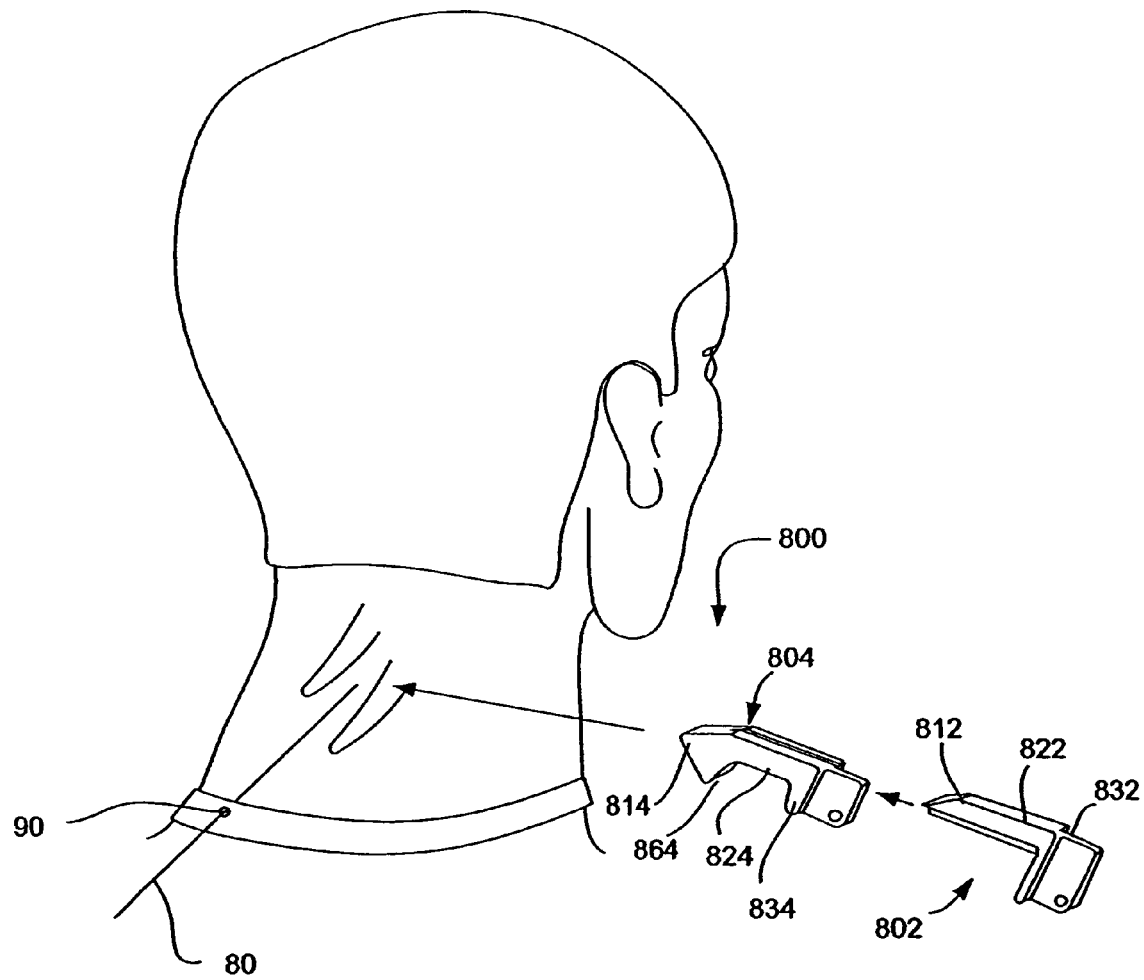
FIG. 20B illustrates an embodiment of a method in accordance with the present invention for implanting the interspinous implant of FIG. 18A.

In other embodiments of methods in accordance with the present invention, the implant can include an initiating piece 804 and a distraction piece 802, such as described above in FIGS. 18A-19E. In such embodiments, as shown in FIG. 20B, preferably a guide wire 80 is inserted through a placement network or guide 90 into the neck of the implant recipient (as shown and described above). Once the guide wire 80 is positioned with the aid of imaging techniques, an incision is made on the side of the neck so that an initiating piece 804 of the implant 800 can be positioned in the neck thorough an incision and along a line that is about perpendicular to the guide wire 80 and directed at the end of the guide wire. The initiating piece 804 can include a lower distraction element 814, the second wing 860, a lower portion 824 of the spacer, and a lower portion 834 of the first wing. The implant 800 is inserted into the neck of the patient, between adjacent spinous processes. Preferably during insertion, the lower distraction element 814 pierces or separates the tissue without severing the tissue, and the implant 800 is positioned so that the upper portion 824 of the spacer is disposed between the adjacent spinous processes.

Once the initiating piece 804 is satisfactorily positioned, a distracting piece 802 can be inserted along a line that is approximately colinear with the line over which the initiating piece 804 is inserted, but positioned so that a rail 882 of the distracting piece 802 mates with a slot 884 of the initiating piece 804. The anatomy of the neck is such that it is most convenient and minimally invasive to enter the neck from the side with respect to the implant 800. The distracting piece 802 can be mated to the initiating piece 804, by pegging the first and second perforations 891,893, through an interference fit, or using a catch 881 and recess 887 as described above, or, alternatively by connecting the distracting piece 804 with the initiating piece 802 using a fastener, or by some other device, as described above.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. An interspinous implant adapted to be arranged between spinous processes, comprising:
   a first member comprising:
      a first wing disposed toward a first longitudinal end;
      a second wing disposed toward a second longitudinal end and longitudinally spaced from the first wing;
      a spacer disposed between the first wing and the second wing;
      a distraction guide at the second end of the interspinous implant;
   a second member adapted to be slidably associated with the first member by sliding along an axis to a fully engaged position;
   wherein the first member includes a lower sliding surface and a lower contact surface; wherein the first wing, the second wing, and a lower portion of the spacer extend from the lower contact surface;
   wherein the second member includes an upper sliding surface and a upper contact surface;
   wherein the first and second members are configured such that, when the second member is coupled to the first member so as to be disposed in the fully engaged position, a theoretical line spaced equidistantly from the first and second wings and oriented perpendicular to the axis passes through the second member and then through the first member, then external to the implant without passing through the second member again, such that each of the first member and the second member form exteriormost surfaces of the implant along the line.

2. The implant of claim 1, further comprising:
   a cavity disposed within at least a portion of the lower sliding surface;
   a protrusion extending from at least a portion of the upper sliding surface;
   wherein when the second member is slidably associated with the first member, the protrusion is received within the cavity.

3. The implant of claim 2, wherein:
   the cavity is a slot having a flange extending from a periphery of the slot; and
   the protrusion is a rail having a flange extending from a periphery of the rail.

4. The implant of claim 1, wherein one or both of the first wing and the second wing are adapted to limit movement of the implant relative to the spinous processes.

5. The implant of claim 3, wherein the rail includes a catch and the slot includes a recess so that when the catch is received within the recess, relative movement of the first and second members is limited.

6. An interspinous implant adapted to be arranged between spinous processes, the implant comprising:
   an initiating piece having a first wing and a second wing;
   a distraction piece that can be slidably associated with the initiating piece so that the distraction piece is disposed over the initiating piece;
   wherein the initiating piece is adapted to be arranged between the spinous processes so that one of the spinous processes is disposed at least partially between the first and second wing;
   wherein the initiating piece is configured to be arranged between the spinous processes before the distraction piece is disposed over the initiating piece;
   a first tab extending from the initiating piece, the first tab having a first perforation;
   a second tab extending from the distraction piece, the second tab having a second perforation;
   wherein when the distraction piece is seated over the initiating piece, the first perforation and second perforation are aligned;
   a peg adapted to be positioned through the first and second perforations;
   wherein movement of the distraction piece relative to the initiating piece is limited when the peg is positioned between the first and second perforations.

7. An interspinous implant adapted to be arranged between spinous processes, the interspinous implant comprising:
   a first wing at a first end of the interspinous implant;
   a second wing;
   a spacer disposed between the first wing and the second wing;
   a distraction guide at the second end of the interspinous implant;
   a lower portion and an upper portion adapted to be slidably associated with one another; wherein the lower portion includes a lower sliding surface and a lower contact surface;
   wherein the first wing, the second wing, a first distraction element, and a lower portion of the spacer extend from the lower contact surface;
   wherein the upper portion includes an upper sliding surface and a upper contact surface;
   wherein a second distraction element and an upper portion of the spacer extend from the upper contact surface;
   the implant further comprising:
      a first tab extending from the lower portion, the first tab having a first perforation;
      a second tab extending from the upper portion, the second tab having a second perforation;
      wherein when the distraction piece is seated over the initiating piece, the first perforation and second perforation are aligned;
      a peg adapted to be positioned through the first and second perforations;
      wherein movement of the upper portion relative to the lower portion is limited when the peg is positioned between the first and second perforations.

* * * * *